(12) United States Patent
Stebbins et al.

(10) Patent No.: US 12,036,304 B2
(45) Date of Patent: Jul. 16, 2024

(54) LOW VISCOSITY EMULSION COSMETIC COMPOSITION

(71) Applicant: L'OREAL, Paris (FR)

(72) Inventors: Nicholas David Stebbins, Clark, NJ (US); David Chan, Edison, NJ (US)

(73) Assignee: L'Oreal, Paris (FR)

( * ) Notice: Subject to any disclaimer, the term of this patent is extended or adjusted under 35 U.S.C. 154(b) by 253 days.

(21) Appl. No.: 17/360,235

(22) Filed: Jun. 28, 2021

(65) Prior Publication Data
US 2022/0409516 A1   Dec. 29, 2022

(51) Int. Cl.
| | | |
|---|---|---|
| *A61K 8/81* | (2006.01) | |
| *A61K 8/06* | (2006.01) | |
| *A61K 8/19* | (2006.01) | |
| *A61K 8/67* | (2006.01) | |
| *A61K 8/73* | (2006.01) | |
| *A61Q 19/00* | (2006.01) | |

(52) U.S. Cl.
CPC ............ *A61K 8/8188* (2013.01); *A61K 8/062* (2013.01); *A61K 8/19* (2013.01); *A61K 8/676* (2013.01);
(Continued)

(58) Field of Classification Search
CPC .. A61K 2300/00; A61K 45/06; A61K 36/185; A61K 8/37; A61K 8/9789; A61K 9/0014; A61K 2800/412; A61K 38/00; A61K 8/922; A61K 8/891; A61K 8/19; A61K 9/0019; A61K 8/11; A61K 8/8152; A61K 8/06; A61K 8/345; A61K 8/25; A61K 9/14; A61K 8/97; A61K 8/35; A61K 36/28; A61K 8/26; A61K 8/585; A61K 9/1652; A61K 47/10; A61K 36/48; A61K 8/29; A61K 8/375; A61K 8/86; A61K 8/31; A61K 8/731; A61K 8/0208; A61K 8/73; A61K 8/042; A61K 8/0241; A61K 8/64; A61K 8/9794; A61K 9/1617; A61K 8/27; A61K 8/42; A61K 2800/413; A61K 9/146; A61K 8/894; A61K 9/1694; A61K 9/06; A61K 31/122; A61K 8/062; A61K 8/39; A61K 8/365; A61K 9/2054; A61K 9/145; A61K 9/1647; A61K 9/0075; A61K 36/53; A61K 47/26; A61K 31/00; A61K 8/02; A61K 31/198; A61K 31/19; A61K 8/671; A61K 36/00; A61K 8/34; A61K 9/1635; A61K 31/355; A61K 8/342; A61K 8/361; A61K 8/676; A61K 2800/522; A61K 8/60; A61K 9/0095; A61K 8/8147; A61K 8/678; A61K 31/375; A61K 9/0056; A61K 47/36; A61K 9/1623; A61K 8/498; A61K 31/192; A61K 47/34; A61K 2800/75; A61K 9/1075; A61K 8/368; A61K 8/347; A61K 8/046; A61K 31/7048; A61K 36/82; A61K 47/02; A61K 31/352; A61K 38/47; A61K 9/10; A61K 2800/43; A61K 47/32; A61K 8/8158; A61K 9/2018; A61K 8/63; A61K 2800/56; A61K 47/44; A61K 2800/52; A61K 2800/28; A61K 9/1611; A61K 9/0024; A61K 9/127; A61K 9/19; A61K 33/00; A61K 33/06; A61K 47/14; A61K 31/05; A61K 8/898; A61K 31/70; A61K 8/92; A61K 33/30; A61K 36/23; A61K 8/064; A61K 2800/31; A61K 31/12; A61K 33/24; A61K 8/8111; A61K 8/4946; A61K 8/88; A61K 47/12; A61K 8/4973; A61K 8/895; A61K 9/4858; A61K 9/5026; A61K 8/40; A61K 31/137; A61K 8/14; A61K 31/573; A61K 47/38; A61K 31/519; A61K 8/466; A61K 36/899; A61K 9/2077; A61K 8/732; A61K 8/416; A61K 9/0053; A61K 9/5192; A61K 8/602; A61K 8/66; A61K 8/90; A61K 36/61; A61K 36/81; A61K 36/752; A61K 8/553; A61K 9/1641; A61K 8/0212; A61K 9/16; A61K 2800/594; A61K 9/5078; A61K 8/87; A61K 9/08; A61K 9/2027; A61K 35/20; A61K 9/2013; A61K 31/56; A61K 9/2095; A61K 9/107; A61K 36/87; A61K 31/195; A61K 36/258; A61K 2800/10; A61K 8/4926; A61K 48/00;
(Continued)

(56) References Cited

U.S. PATENT DOCUMENTS

| | | | | |
|---|---|---|---|---|
| 2009/0098171 | A1* | 4/2009 | Alard .................. | A61K 8/731 424/401 |
| 2010/0331429 | A1* | 12/2010 | Lorant ................. | A61K 8/73 514/777 |
| 2017/0304173 | A1* | 10/2017 | Elder .................. | A61K 8/466 |
| 2020/0038314 | A1 | 2/2020 | Berge et al. | |

FOREIGN PATENT DOCUMENTS

EP   3615148 B1 *   7/2022   .............. A61Q 5/00

OTHER PUBLICATIONS

Mintel, "Lab Series Skincare for Men Moisturize—Rescue Water Emulsion", Record ID No. 8067299, published Aug. 2020, www.gnpd.com.

(Continued)

*Primary Examiner* — Audrea B Coniglio
(74) *Attorney, Agent, or Firm* — McNees Wallace & Nurick

(57) ABSTRACT

The salt-stable cosmetic composition is in the form of a low viscosity emulsion (oil in water) and is especially stable at high electrolyte contents and includes a salt-stable polymeric system comprising a polymer blend such that the salt-stable cosmetic composition resists phase separation, pilling and gellifying at high salt content, conferring a flowable, lightweight lotion-type texture.

19 Claims, No Drawings

(52) U.S. Cl.
CPC ............... *A61K 8/73* (2013.01); *A61K 8/8147* (2013.01); *A61Q 19/00* (2013.01); *A61K 2800/10* (2013.01); *A61K 2800/48* (2013.01); *A61K 2800/52* (2013.01)

(58) Field of Classification Search
CPC .......... A61K 38/465; A61K 8/28; A61K 8/49; A61K 8/463; A61K 2800/262; A61K 9/0073; A61K 9/0043; A61K 31/496; A61K 31/704; A61K 9/006; A61K 8/85; A61K 31/715; A61K 47/24; A61K 8/0229; A61K 38/28; A61K 9/1688; A61K 9/5153; A61K 2800/782; A61K 31/353; A61K 31/045; A61K 9/0048; A61K 9/2009; A61K 9/5084; A61K 31/202; A61K 8/41; A61K 31/337; A61K 8/8182; A61K 36/886; A61K 9/2081; A61K 9/5031; A61K 9/5146; A61K 31/07; A61K 47/42; A61K 8/4966; A61K 36/484; A61K 33/04; A61K 9/2866; A61K 36/54; A61K 31/485; A61K 9/143; A61K 36/9068; A61K 9/1676; A61K 2800/57; A61K 38/4873; A61K 31/165; A61K 36/45; A61K 36/73; A61K 31/167; A61K 36/03; A61K 36/889; A61K 31/58; A61K 8/445; A61K 8/65; A61K 9/5161; A61K 8/22; A61K 8/735; A61K 31/455; A61K 36/9066; A61K 9/5123; A61K 36/16; A61K 38/1709; A61K 36/31; A61K 9/008; A61K 8/55; A61K 9/5089; A61K 31/525; A61K 8/24; A61K 8/36; A61K 9/5073; A61K 47/183; A61K 31/20; A61K 31/205; A61K 8/044; A61K 9/1658; A61K 31/60; A61K 9/5138; A61K 2800/5426; A61K 8/68; A61K 31/522; A61K 36/88; A61K 31/44; A61K 39/00; A61K 9/5047; A61K 31/385; A61K 47/22; A61K 8/494; A61K 2800/88; A61K 31/216; A61K 36/02; A61K 9/5115; A61K 36/38; A61K 38/48; A61K 9/167; A61K 9/4866; A61K 31/57; A61K 31/714; A61K 8/737; A61K 31/405; A61K 31/40; A61K 8/645; A61K 31/575; A61K 8/025; A61K 36/47; A61K 8/9728; A61K 8/925; A61K 8/4953; A61K 8/442; A61K 9/7007; A61K 8/46; A61K 8/0279; A61K 8/67; A61K 36/74; A61K 47/20; A61K 31/135; A61K 35/12; A61K 8/84; A61K 9/4808; A61K 36/71; A61K 47/60; A61K 8/20; A61K 8/817; A61K 31/4415; A61K 8/23; A61K 8/4913; A61K 2800/92; A61K 36/42; A61K 9/2059; A61K 38/4886; A61K 38/44; A61K 9/12; A61K 2039/505; A61K 2800/651; A61K 36/534; A61K 8/675; A61K 31/685; A61K 2800/54; A61K 2800/654; A61K 9/0078; A61K 39/39; A61K 36/736; A61K 9/0034; A61K 36/63; A61K 8/068; A61K 31/445; A61K 36/05; A61K 2800/70; A61K 9/1682; A61K 8/355; A61K 8/0216; A61K 8/893; A61K 8/927; A61K 8/8176; A61K 31/4745; A61K 8/33; A61K 31/197; A61K 38/39; A61K 9/5015; A61K 2800/59; A61K 47/06; A61K 9/20; A61K 31/015; A61K 31/4439; A61K 33/42; A61K 8/604; A61K 31/7088; A61K 35/60; A61K 38/482; A61K 31/366; A61K 31/495; A61K 8/892; A61K 8/9711; A61K 8/8117; A61K 2800/596; A61K 31/138; A61K 31/404; A61K 31/55; A61K 36/232; A61K 31/22; A61K 31/35; A61K 31/555; A61K 2800/21; A61K 8/89; A61K 47/6923; A61K 31/365; A61K 36/8962; A61K 36/537; A61K 31/047; A61K 2800/48; A61K 8/8129; A61K 9/0007; A61K 2800/87; A61K 36/481; A61K 8/0245; A61K 38/49; A61K 8/8164; A61K 9/007; A61K 33/26; A61K 8/362; A61K 9/5169; A61K 8/99; A61K 36/15; A61K 9/209; A61K 47/46; A61K 31/201; A61K 33/34; A61K 9/5036; A61K 36/539; A61K 36/67; A61K 8/022; A61K 31/415; A61K 8/9706; A61K 9/1272; A61K 9/205; A61K 31/51; A61K 31/675; A61K 36/896; A61K 9/7015; A61K 2039/55555; A61K 38/08; A61K 31/7076; A61K 36/68; A61K 38/27; A61K 9/2031; A61K 36/77; A61K 31/14; A61K 39/12; A61K 9/1271; A61K 9/2846; A61K 2800/524; A61K 38/4826; A61K 8/733; A61K 31/185; A61K 8/04; A61K 9/50; A61K 2800/5922; A61K 2800/624; A61K 31/43; A61K 31/59; A61K 9/5042; A61K 31/437; A61K 31/7004; A61K 36/06; A61K 8/736; A61K 31/505; A61K 31/16; A61K 8/70; A61K 8/027; A61K 36/704; A61K 36/76; A61K 9/0009; A61K 47/18; A61K 35/747; A61K 36/27; A61K 31/155; A61K 36/24; A61K 38/45; A61K 9/48; A61K 47/6929; A61K 31/194; A61K 31/65; A61K 31/728; A61K 33/38; A61K 31/439; A61K 8/738; A61K 9/51; A61K 31/593; A61K 9/4891; A61K 36/30; A61K 31/203; A61K 38/43; A61K 2800/621; A61K 2800/592; A61K 8/606; A61K 8/066; A61K 2800/30; A61K 31/407; A61K 31/436; A61K 36/65; A61K 38/18; A61K 2236/00; A61K 31/66; A61K 31/4985; A61K 47/62; A61K 2800/436; A61K 36/324; A61K 36/55; A61K 38/54; A61K 36/07; A61K 31/565; A61K 38/13; A61K 8/673; A61K 31/737; A61K 38/57; A61K 31/53; A61K 36/22; A61K 36/80; A61K 36/282; A61K 8/9767; A61K 2800/244; A61K 31/215; A61K 35/74; A61K 8/965; A61K 8/9771; A61K 9/00; A61K 31/7008; A61K 9/501; A61K 41/0052; A61K 31/74; A61K 8/0204; A61K 8/21; A61K 2800/805; A61K 36/21; A61K 8/0295; A61K 8/492; A61K 38/16; A61K 8/4986; A61K 2800/51; A61K 31/47; A61K 36/04; A61K 8/447; A61K 31/23; A61K 33/14; A61K 31/727; A61K 31/34; A61K 47/61; A61K 2800/33; A61K 31/473; A61K 9/5052; A61K 31/196; A61K 31/27; A61K 35/644; A61K 8/0254; A61K 8/03; A61K 8/4993; A61K 31/01; A61K 35/32;

A61K 9/70; A61K 31/5377; A61K
38/446; A61K 8/9717; A61K 8/987;
A61K 31/4045; A61K 8/38; A61K
8/9722; A61K 36/79; A61K 31/551;
A61K 33/32; A61K 38/23; A61K 38/063;
A61K 38/40; A61K 9/0004; A61K
2800/5424; A61K 36/75; A61K 38/1825;
A61K 31/4196; A61K 33/243; A61K
38/1841; A61K 41/0004; A61K 36/738;
A61K 8/897; A61K 9/1277; A61K
41/0028; A61K 8/43; A61K 31/713;
A61K 33/08; A61K 2800/884; A61K
2800/91; A61K 36/41; A61K 2800/81;
A61K 33/40; A61K 35/28; A61K 47/54;
A61K 8/0283; A61K 38/17; A61K
2800/58; A61K 31/28; A61K 38/4813;
A61K 31/765; A61K 38/212; A61K 8/72;
A61K 8/496; A61K 9/0031; A61K 31/09;
A61K 36/11; A61K 36/286; A61K 38/51;
A61K 9/4825; A61K 31/343; A61K
9/2886; A61K 31/17; A61K 36/254;
A61K 36/58; A61K 31/513; A61K
36/708; A61K 36/8945; A61K 8/91;
A61K 9/2072; A61K 8/58; A61K 9/0021;
A61K 9/0063; A61K 36/815; A61K
31/4188; A61K 31/506; A61K 31/52;
A61K 2800/85; A61K 36/19; A61K
31/4164; A61K 35/745; A61K 36/328;
A61K 8/986; A61K 31/235; A61K
31/401; A61K 31/421; A61K 31/7068;
A61K 33/10; A61K 31/4709; A61K
36/355; A61K 38/38; A61K 39/395;
A61K 47/6937; A61K 35/748; A61K
9/7023; A61K 33/18; A61K 8/8135;
A61K 31/341; A61K 31/517; A61K
47/64; A61K 31/423; A61K 36/14; A61K
31/785; A61K 31/49; A61K 35/36; A61K
36/734; A61K 36/906; A61K 38/09;
A61K 39/3955; A61K 8/982; A61K
2800/5422; A61K 31/5517; A61K 47/593;
A61K 31/427; A61K 47/40; A61K
47/6925; A61K 8/4933; A61K 31/422;
A61K 31/426; A61K 38/018; A61K
47/6935; A61K 2039/53; A61K 36/718;
A61K 9/28; A61K 49/0002; A61K
9/0058; A61K 2800/242; A61K 2800/42;
A61K 2800/652; A61K 31/5415; A61K
31/5513; A61K 47/6951; A61K 9/1664;
A61K 31/225; A61K 36/804; A61K
2800/622; A61K 31/4178; A61K 31/501;
A61K 31/695; A61K 36/35; A61K 36/84;
A61K 47/6927; A61K 51/1244; A61K
2800/434; A61K 31/616; A61K 36/064;
A61K 38/05; A61K 49/0093; A61K
49/223; A61K 2800/94; A61K 36/284;
A61K 38/21; A61K 8/8123; A61K
9/5094; A61K 2800/95; A61K 31/13;
A61K 31/351; A61K 35/57; A61K 9/122;
A61K 38/46; A61K 8/9761; A61K 31/46;
A61K 35/50; A61K 38/06; A61K
38/4893; A61K 31/327; A61K 36/18;
A61K 38/10; A61K 31/164; A61K
31/335; A61K 31/722; A61K 36/29;
A61K 36/59; A61K 36/85; A61K
39/0011; A61K 9/113; A61K 33/44;
A61K 36/235; A61K 36/746; A61K
38/1875; A61K 8/899; A61K 9/1274;
A61K 36/70; A61K 38/22; A61K 41/00;
A61K 47/58; A61K 8/988; A61K 9/4816;
A61K 9/4875; A61K 2800/872; A61K
38/443; A61K 31/7016; A61K 31/7105;
A61K 36/725; A61K 9/0051; A61K
35/744; A61K 36/605; A61K 38/168;
A61K 38/26; A61K 38/30; A61K 38/488;
A61K 9/02; A61K 2039/542; A61K
31/315; A61K 31/381; A61K 31/475;
A61K 31/7072; A61K 38/1866; A61K
47/08; A61K 35/741; A61K 36/296;
A61K 8/411; A61K 31/7024; A61K
33/22; A61K 31/7036; A61K 47/186;
A61K 47/28; A61K 8/69; A61K
2236/333; A61K 2800/623; A61K 38/193;
A61K 38/4833; A61K 2800/614; A61K
31/454; A61K 31/7056; A61K 36/60;
A61K 47/6911; A61K 31/545; A61K
31/7052; A61K 47/549; A61K 9/0085;
A61K 9/141; A61K 9/2086; A61K
2800/612; A61K 2800/63; A61K 31/282;
A61K 35/34; A61K 36/074; A61K
36/488; A61K 47/6921; A61K 8/0275;
A61K 31/232; A61K 31/357; A61K
31/4166; A61K 31/568; A61K 36/288;
A61K 36/898; A61K 38/50; A61K
9/4833; A61K 31/085; A61K 36/076;
A61K 36/25; A61K 9/0046; A61K
9/0065; A61K 2800/222; A61K 31/10;
A61K 31/4375; A61K 31/557; A61K
31/702; A61K 31/7028; A61K 31/726;
A61K 36/33; A61K 36/489; A61K
36/756; A61K 36/888; A61K 38/19;
A61K 2039/545; A61K 2039/55566;
A61K 31/42; A61K 31/661; A61K
31/7034; A61K 8/81; A61K 9/0092;
A61K 2039/55505; A61K 31/11; A61K
31/78; A61K 33/244; A61K 41/0057;
A61K 47/645; A61K 31/4174; A61K
33/242; A61K 36/062; A61K 9/282;
A61K 2800/591; A61K 31/41; A61K
31/4184; A61K 31/4545; A61K 38/12;
A61K 48/0041; A61K 31/37; A61K
35/30; A61K 36/66; A61K 38/07; A61K
38/1858; A61K 8/0237; A61K 2039/54;
A61K 31/435; A61K 31/535; A61K
36/13; A61K 36/236; A61K 36/482;
A61K 38/02; A61K 31/191; A61K
9/2853; A61K 9/7084; A61K 31/465;
A61K 31/716; A61K 35/16; A61K 35/38;
A61K 36/535; A61K 38/29; A61K
8/0233; A61K 9/284; A61K 9/485;
A61K 8/556; A61K 31/133; A61K 31/425;
A61K 31/711; A61K 35/22; A61K
36/8965; A61K 31/4422; A61K 35/62;
A61K 47/6949; A61K 31/277; A61K
31/5575; A61K 38/164; A61K 38/1808;
A61K 39/145; A61K 47/59; A61K
47/6907; A61K 31/245; A61K 36/8998;
A61K 31/24; A61K 36/39; A61K 36/575;
A61K 38/4846; A61K 47/542; A61K
8/9741; A61K 2039/6093; A61K 2800/49;
A61K 31/7012; A61K 9/2068; A61K

2039/541; A61K 2236/39; A61K 31/221; A61K 31/635; A61K 35/76; A61K 39/385; A61K 48/0075; A61K 9/0026; A61K 2039/55511; A61K 2236/331; A61K 2800/83; A61K 31/4412; A61K 31/498; A61K 36/17; A61K 38/166; A61K 38/1816; A61K 8/8141; A61K 2236/33; A61K 2800/5428; A61K 2800/74; A61K 31/095; A61K 31/21; A61K 36/37; A61K 38/191; A61K 47/50; A61K 47/6903; A61K 6/20; A61K 9/7061; A61K 2800/78; A61K 2800/882; A61K 31/4402; A61K 36/36; A61K 36/52; A61K 38/005; A61K 49/00; A61K 8/45; A61K 31/80; A61K 9/7053; A61K 31/54; A61K 31/717; A61K 36/40; A61K 38/25; A61K 38/363; A61K 8/0291; A61K 9/2893; A61K 2039/55561; A61K 31/18; A61K 31/397; A61K 31/4172; A61K 31/665; A61K 35/545; A61K 36/49; A61K 38/55; A61K 47/6939; A61K 31/136; A61K 31/231; A61K 36/234; A61K 38/185; A61K 47/544; A61K 47/6931; A61K 8/0225; A61K 8/415; A61K 9/1273; A61K 36/64; A61K 2035/128; A61K 2800/26; A61K 31/4418; A61K 9/286; A61K 9/5057; A61K 31/4704; A61K 35/35; A61K 35/612; A61K 36/344; A61K 36/62; A61K 36/8994; A61K 39/35; A61K 47/30; A61K 47/6901; A61K 9/009; A61K 31/125; A61K 31/444; A61K 31/4458; A61K 31/663; A61K 35/39; A61K 35/742; A61K 36/287; A61K 36/538; A61K 38/2278; A61K 38/484; A61K 48/0008; A61K 49/0004; A61K 49/0054; A61K 8/0258; A61K 8/0266; A61K 2236/15; A61K 31/683; A61K 35/618; A61K 39/21; A61K 41/0071; A61K 47/543; A61K 49/1818; A61K 9/2063; A61K 9/2813; A61K 2039/543; A61K 31/395; A61K 31/4468; A61K 31/585; A61K 31/69; A61K 35/02; A61K 47/643; A61K 8/981; A61K 9/148; A61K 9/204; A61K 31/567; A61K 36/882; A61K 38/20; A61K 38/37; A61K 48/005; A61K 8/8194; A61K 31/497; A61K 35/407; A61K 36/315; A61K 36/51; A61K 36/515; A61K 36/638; A61K 38/14; A61K 38/36; A61K 47/585; A61K 2236/30; A61K 2236/37; A61K 36/72; A61K 38/42; A61K 8/0287; A61K 8/985; A61K 9/124; A61K 9/703; A61K 2800/438; A61K 31/4406; A61K 31/5383; A61K 31/7032; A61K 39/0005; A61K 8/4906; A61K 2800/72; A61K 31/145; A61K 31/4015; A61K 31/5375; A61K 36/46; A61K 36/69; A61K 38/1767; A61K 39/39558; A61K 9/1629; A61K 9/5068; A61K 2039/57; A61K 2236/51; A61K 31/4525; A61K 31/4535; A61K 36/78; A61K 38/2013; A61K 49/0043; A61K 9/0097; A61K 9/2004; A61K 2039/552; A61K 2800/24; A61K 2800/61; A61K 31/724; A61K 35/14; A61K 36/233; A61K 38/1793; A61K 41/0038; A61K 6/69; A61K 8/896; A61K 9/0002; A61K 2800/47; A61K 2800/77; A61K 31/075; A61K 31/336; A61K 35/08; A61K 36/068; A61K 38/385; A61K 2039/55583; A61K 31/166; A61K 31/4025; A61K 35/63; A61K 36/505; A61K 36/714; A61K 36/8969; A61K 47/52; A61K 47/6415; A61K 47/68; A61K 47/6849; A61K 49/0032; A61K 49/227; A61K 2039/55544; A61K 2039/70; A61K 2800/874; A61K 31/554; A61K 31/5685; A61K 36/90; A61K 38/2235; A61K 9/1605; A61K 2039/55516; A61K 31/33; A61K 31/734; A61K 35/44; A61K 36/238; A61K 36/56; A61K 36/8964; A61K 39/0008; A61K 47/6933; A61K 9/0087; A61K 31/121; A61K 33/16; A61K 36/43; A61K 36/532; A61K 36/748; A61K 8/96; A61K 9/0041; A61K 2035/124; A61K 2039/55572; A61K 31/451; A61K 31/569; A61K 35/54; A61K 35/616; A61K 36/346; A61K 38/162; A61K 38/177; A61K 38/1891; A61K 38/31; A61K 39/08; A61K 45/00; A61K 47/551; A61K 49/0056; A61K 8/9783; A61K 9/5063; A61K 2800/86; A61K 31/592; A61K 31/655; A61K 31/6615; A61K 31/721; A61K 47/65; A61K 6/17; A61K 8/315; A61K 8/608; A61K 9/2036; A61K 9/5021; A61K 2039/55522; A61K 2039/55588; A61K 2800/20; A61K 2800/41; A61K 31/30; A61K 31/48; A61K 35/33; A61K 39/245; A61K 49/0021; A61K 6/30; A61K 2121/00; A61K 31/4355; A61K 31/4365; A61K 31/4725; A61K 35/00; A61K 36/424; A61K 36/716; A61K 38/095; A61K 49/049; A61K 8/30; A61K 2236/35; A61K 31/26; A61K 31/403; A61K 31/7084; A61K 31/7135; A61K 33/20; A61K 36/536; A61K 36/758; A61K 38/1703; A61K 38/215; A61K 9/0036; A61K 31/222; A61K 31/438; A61K 31/4425; A61K 31/4965; A61K 31/718; A61K 35/51; A61K 36/34; A61K 36/9064; A61K 38/1833; A61K 41/0042; A61K 47/55; A61K 8/8105; A61K 9/1275; A61K 2123/00; A61K 2800/45; A61K 2800/546; A61K 31/50; A61K 31/736; A61K 36/09; A61K 36/533; A61K 38/014; A61K 38/56; A61K 47/541; A61K 2800/437; A61K 31/15; A61K 31/275; A61K 31/4436; A61K 35/13; A61K 36/808; A61K 38/03; A61K 49/0041; A61K 51/12; A61K 31/02; A61K 31/4748; A61K 31/536; A61K 31/538; A61K 31/618; A61K 36/428; A61K 36/57; A61K 36/884; A61K 36/8967; A61K 38/04; A61K 49/0008; A61K 51/088; A61K 51/1255; A61K 8/418; A61K 9/0017; A61K 2039/5154; A61K 2039/5252; A61K 2800/84; A61K 31/428; A61K 31/64; A61K 31/688;

A61K 35/55; A61K 35/66; A61K 38/01;
A61K 38/24; A61K 39/292; A61K
49/0017; A61K 49/0084; A61K 49/225;
A61K 9/0012; A61K 9/0082; A61K
9/5176; A61K 31/08; A61K 31/38; A61K
31/553; A61K 31/606; A61K 31/662;
A61K 35/15; A61K 35/24; A61K 36/44;
A61K 36/634; A61K 47/595; A61K
47/6851; A61K 49/0065; A61K 8/0262;
A61K 8/18; A61K 9/1278; A61K 9/2826;
A61K 2039/555; A61K 2039/55577;
A61K 2039/622; A61K 31/131; A61K
31/409; A61K 31/4409; A61K 31/566;
A61K 31/706; A61K 31/7115; A61K
36/487; A61K 36/8905; A61K 38/011;
A61K 47/646; A61K 49/0423; A61K
2800/22; A61K 2800/34; A61K 2800/60;
A61K 31/295; A61K 31/4706; A61K
31/472; A61K 31/63; A61K 33/12; A61K
33/28; A61K 35/413; A61K 36/8968;
A61K 38/208; A61K 38/486; A61K
38/53; A61K 38/556; A61K 39/39591;
A61K 49/1806; A61K 9/7092; A61K
2035/126; A61K 2236/53; A61K 2800/80;
A61K 31/4741; A61K 31/546; A61K
33/245; A61K 36/483; A61K 38/2242;
A61K 38/52; A61K 39/0003; A61K
47/6957; A61K 49/0428; A61K 9/7069;
A61K 2039/5258; A61K 2039/60; A61K
2236/17; A61K 31/433; A61K 31/549;
A61K 31/733; A61K 31/745; A61K
31/77; A61K 31/795; A61K 36/744;
A61K 36/8984; A61K 38/012; A61K
47/545; A61K 47/554; A61K 47/67;
A61K 49/1866; A61K 49/22; A61K
51/10; A61K 6/838; A61K 8/983; A61K
9/513; A61K 9/7076; A61K 2800/82;
A61K 31/132; A61K 31/36; A61K
31/417; A61K 31/4192; A61K 35/614;
A61K 35/655; A61K 36/32; A61K
38/1774; A61K 47/56; A61K 48/0033;
A61K 49/0067; A61K 49/04; A61K
49/226; A61K 51/065; A61K 51/1251;
A61K 9/4841; A61K 2039/5254; A61K
31/4152; A61K 31/4168; A61K 31/424;
A61K 33/36; A61K 35/64; A61K 36/268;
A61K 36/8988; A61K 47/665; A61K
47/6803; A61K 47/6891; A61K 47/6915;
A61K 49/0091; A61K 49/1833; A61K
49/222; A61K 2039/5156; A61K 2236/19;
A61K 31/223; A61K 31/453; A61K
31/708; A61K 31/732; A61K 36/10;
A61K 36/9062; A61K 38/046; A61K
38/204; A61K 47/16; A61K 47/642;
A61K 47/6811; A61K 48/0025; A61K
49/0006; A61K 49/0452; A61K 49/085;
A61K 49/186; A61K 8/00; A61K 8/9733;
A61K 9/288; A61K 2039/507; A61K
2039/51; A61K 2039/5158; A61K
2039/5256; A61K 2039/6087; A61K
2800/40; A61K 2800/548; A61K 31/025;
A61K 35/19; A61K 35/37; A61K 36/86;
A61K 38/195; A61K 38/2066; A61K
38/225; A61K 38/33; A61K 39/39508;
A61K 41/0061; A61K 49/0419; A61K
49/1863; A61K 51/0497; A61K 2035/115;
A61K 2039/6037; A61K 31/175; A61K
35/68; A61K 36/486; A61K 36/8888;
A61K 38/4866; A61K 39/155; A61K
39/39541; A61K 41/0047; A61K 48/0083;
A61K 48/0091; A61K 49/12; A61K
2039/575; A61K 31/382; A61K 31/515;
A61K 31/664; A61K 31/739; A61K
31/787; A61K 38/1741; A61K 38/217;
A61K 39/102; A61K 39/40; A61K 47/00;
A61K 47/555; A61K 47/6899; A61K
51/08; A61K 51/1093; A61K 6/35; A61K
2039/522; A61K 31/065; A61K 31/443;
A61K 31/45; A61K 31/738; A61K 35/10;
A61K 35/17; A61K 35/26; A61K 36/237;
A61K 36/264; A61K 36/754; A61K
38/066; A61K 38/2207; A61K 38/2292;
A61K 38/58; A61K 39/001; A61K 39/05;
A61K 47/6897; A61K 49/048; A61K
49/1815; A61K 49/1887; A61K 6/887;
A61K 9/5005; A61K 2035/122; A61K
2039/55594; A61K 2039/585; A61K
2236/31; A61K 2800/432; A61K 31/431;
A61K 31/4453; A61K 31/541; A61K
31/731; A61K 31/75; A61K 35/58; A61K
36/835; A61K 39/15; A61K 41/17; A61K
47/547; A61K 47/6801; A61K 47/6855;
A61K 48/0066; A61K 49/0082; A61K
49/10; A61K 49/1812; A61K 49/1824;
A61K 49/1845; A61K 49/1854; A61K
8/9778; A61K 31/416; A61K 35/04;
A61K 35/42; A61K 35/52; A61K 36/12;
A61K 36/26; A61K 38/1729; A61K
38/202; A61K 38/34; A61K 39/0013;
A61K 39/02; A61K 39/0258; A61K
39/095; A61K 47/6905; A61K 47/6913;
A61K 47/6941; A61K 49/0013; A61K
49/0058; A61K 49/0404; A61K 49/0438;
A61K 49/0485; A61K 49/1881; A61K
51/0491; A61K 6/884; A61K 8/98; A61K
9/4883; A61K 2039/515; A61K 2039/521;
A61K 2039/525; A61K 2039/605; A61K
2800/526; A61K 31/04; A61K 31/06;
A61K 31/255; A61K 31/4155; A61K
31/4353; A61K 31/502; A61K 31/7064;
A61K 36/83; A61K 38/1732; A61K
38/1761; A61K 39/39533; A61K 39/44;
A61K 47/548; A61K 49/0036; A61K
49/1836; A61K 49/1857; A61K 51/1213;
A61K 6/65; A61K 8/9739; A61K
2039/5152; A61K 2039/6031; A61K
2039/627; A61K 31/4427; A61K 31/4433;
A61K 33/02; A61K 35/65; A61K 38/35;
A61K 39/04; A61K 41/0033; A61K
47/552; A61K 47/6425; A61K 47/66;
A61K 47/6898; A61K 49/0034; A61K
49/126; A61K 49/18; A61K 6/54; A61K
9/5107; A61K 9/5184; A61K 2039/577;
A61K 2039/6006; A61K 2039/6018;
A61K 2039/62; A61K 31/265; A61K
31/537; A61K 31/723; A61K 31/79;
A61K 35/583; A61K 35/763; A61K
36/50; A61K 36/739; A61K 36/8966;
A61K 38/043; A61K 38/178; A61K
38/196; A61K 38/2006; A61K 38/2053;

A61K 38/2086; A61K 38/2271; A61K 39/001102; A61K 39/001156; A61K 39/001186; A61K 39/015; A61K 39/099; A61K 41/009; A61K 47/644; A61K 47/6889; A61K 49/0052; A61K 49/0442; A61K 51/1027; A61K 51/1045; A61K 51/1217; A61K 6/52; A61K 9/2806; A61K 2039/544; A61K 2039/572; A61K 2800/62; A61K 31/055; A61K 31/25; A61K 31/325; A61K 31/658; A61K 31/729; A61K 35/18; A61K 35/586; A61K 35/761; A61K 36/732; A61K 38/2026; A61K 38/395; A61K 39/0002; A61K 39/0006; A61K 39/00117; A61K 39/0208; A61K 39/0241; A61K 39/0275; A61K 39/07; A61K 39/36; A61K 39/42; A61K 47/6893; A61K 49/006; A61K 49/1821; A61K 49/183; A61K 49/1869; A61K 51/1227; A61K 6/70; A61K 6/864; A61K 9/025; A61K 9/2833; A61K 9/7038; A61K 2035/11; A61K 2039/55533; A61K 2039/64; A61K 2236/55; A61K 31/712; A61K 33/241; A61K 35/48; A61K 35/56; A61K 36/855; A61K 38/1751; A61K 38/4806; A61K 39/001106; A61K 39/001191; A61K 39/165; A61K 47/557; A61K 47/6809; A61K 47/6815; A61K 47/6839; A61K 47/6953; A61K 48/0058; A61K 49/0461; A61K 49/14; A61K 49/1848; A61K 51/0402; A61K 51/1206; A61K 51/1241; A61K 51/1296; A61K 6/00; A61K 6/836; A61K 6/891; A61K 8/9755; A61K 9/1276; A61K 2039/523; A61K 2039/58; A61K 2236/10; A61K 2800/00; A61K 2800/544; A61K 31/03; A61K 31/105; A61K 31/4743; A61K 31/529; A61K 31/5355; A61K 31/542; A61K 31/5578; A61K 31/7042; A61K 36/904; A61K 38/085; A61K 39/001158; A61K 39/001182; A61K 39/001184; A61K 39/085; A61K 41/0066; A61K 41/0095; A61K 47/6435; A61K 47/6807; A61K 47/6843; A61K 47/6853; A61K 49/0039; A61K 49/0063; A61K 49/1809; A61K 49/1839; A61K 51/1048; A61K 6/50; A61K 6/853; A61K 8/8188; A61K 9/0029; A61K 9/0068; A61K 9/2022; A61K 2039/517; A61K 2039/55538; A61K 2039/6012; A61K 2039/6075; A61K 2236/13; A61K 2236/50; A61K 2800/65; A61K 31/29; A61K 31/32; A61K 31/4035; A61K 31/4245; A61K 31/5025; A61K 31/67; A61K 36/20; A61K 36/89; A61K 38/15; A61K 38/1706; A61K 38/1722; A61K 38/1735; A61K 38/2257; A61K 38/4853; A61K 39/0007; A61K 39/001188; A61K 39/001194; A61K 39/001195; A61K 39/002; A61K 39/0233; A61K 39/092; A61K 39/235; A61K 39/29; A61K 45/05; A61K 47/51; A61K 47/6455; A61K 47/6829; A61K 47/6871; A61K 47/6885; A61K 47/69; A61K 47/6917; A61K 49/0045; A61K 49/0047; A61K 49/0409; A61K 51/109; A61K 6/78; A61K 9/2045; A61K 2039/55; A61K 2039/6043; A61K 2039/80; A61K 2800/542; A61K 31/035; A61K 31/5365; A61K 35/06; A61K 36/342; A61K 36/8884; A61K 38/2264; A61K 39/001162; A61K 39/001171; A61K 39/098; A61K 39/275; A61K 39/285; A61K 41/0023; A61K 41/008; A61K 47/6817; A61K 47/6877; A61K 47/6879; A61K 47/6919; A61K 49/0089; A61K 49/1803; A61K 51/1063; A61K 51/1096; A61K 51/1234; A61K 6/40; A61K 6/77; A61K 6/898; A61K 9/2873; A61K 2039/6025; A61K 2039/892; A61K 31/4465; A61K 31/499; A61K 31/4995; A61K 31/559; A61K 31/612; A61K 31/621; A61K 31/7125; A61K 35/646; A61K 35/766; A61K 36/195; A61K 36/485; A61K 36/8895; A61K 38/017; A61K 38/105; A61K 38/1725; A61K 38/1738; A61K 38/1777; A61K 38/179; A61K 38/2221; A61K 39/001151; A61K 39/001166; A61K 39/001181; A61K 39/001192; A61K 39/012; A61K 39/0216; A61K 39/107; A61K 39/13; A61K 47/556; A61K 47/641; A61K 47/6835; A61K 47/6845; A61K 47/6857; A61K 47/6867; A61K 47/6869; A61K 47/6909; A61K 49/001; A61K 49/005; A61K 49/0073; A61K 49/0414; A61K 49/0476; A61K 49/1827; A61K 49/1878; A61K 49/189; A61K 51/00; A61K 51/04; A61K 51/0417; A61K 51/0459; A61K 51/048; A61K 51/0489; A61K 51/0495; A61K 51/1203; A61K 51/1282; A61K 6/71; A61K 6/74; A61K 6/75; A61K 6/816; A61K 31/39; A61K 31/429; A61K 31/4515; A61K 31/4738; A61K 31/5545; A61K 31/5585; A61K 31/609; A61K 31/775; A61K 35/648; A61K 36/066; A61K 36/894; A61K 38/1754; A61K 38/32; A61K 38/553; A61K 39/0001; A61K 39/0015; A61K 39/0225; A61K 39/0283; A61K 39/118; A61K 39/175; A61K 41/0076; A61K 47/558; A61K 47/605; A61K 47/6863; A61K 47/6865; A61K 47/6873; A61K 49/0095; A61K 49/0097; A61K 49/0471; A61K 49/06; A61K 49/128; A61K 49/146; A61K 49/16; A61K 49/1842; A61K 49/1851; A61K 51/0482; A61K 51/082; A61K 51/1224; A61K 51/1258; A61K 51/1265; A61K 6/56; A61K 6/62; A61K 6/824; A61K 6/889; A61K 9/7046; A61K 8/44; A61Q 19/08; A61Q 1/04; A61Q 17/04; A61Q 19/00; A61Q 1/10; A61Q 1/00

See application file for complete search history.

(56) References Cited

OTHER PUBLICATIONS

Mintel, "Lab Series Skincare for Men Moisturize Rescue Water—Emulsion", Record ID No. 7969043, published Aug. 2020, www.gnpd.com.

(56) References Cited

OTHER PUBLICATIONS

Mintel, "Lab Series Skincare for Men Moisturize Rescue Water—Emulsion", Record ID No. 7933589, published Jul. 2020, www.gnpd.com.
Mintel, "Lab Series Skincare for Men Moisturize—Rescue Water Emulsion", Record ID No. 7618691, published May 2020, www.gnpd.com.
Mintel, "Estee Lauder Holiday 2019—12 Days of Beauty", Record ID No. 7133827, published Dec. 2019, www.gnpd.com.
Mintel, "Estee Lauder Christmas 2019—12 Days of Beauty", Record ID No. 7103533, published Dec. 2019, www.gnpd.com.
Mintel, "Murad Age Reform—Joyful & Rejuvenated Set", Record ID No. 5344175, published Dec. 2017, www.gnpd.com.
Mintel, "La Mer—The Moisturizing Matte Lotion", Record ID No. 5039225, published Aug. 2017, www.gnpd.com.
Mintel, "La Mer—The Moisturizing Matte Lotion", Record ID No. 5039229, published Aug. 2017, www.gnpd.com.
Mintel, "La Mer—The Moisturizing Matte Lotion", Record ID No. 4892643, published Jul. 2017, www.gnpd.com.
Mintel, Anonymous, "Daily Tone Up Sun Block SPF50+ PA++++" ID No. 6602251, XP055731348, Jun. 6, 2019.
Mintel, Anonymous, "Sheer Cream" ID No. 5925293, XP055650853, Aug. 23, 2018.
Mintel, Anonymous, "Sym-Micro Essence" ID No. 7607177, XP055776740, May 19, 2020.
Anonymous, "Utilisation de l'epaississant Sepimax Zen pour preparer des formulation cosmetiques parfumantes" XP013155086, Dec. 5, 2012.
Search Report issued to French counterpart Application No. FR2108837 dated May 9, 2022.

\* cited by examiner

LOW VISCOSITY EMULSION COSMETIC COMPOSITION

FIELD OF THE INVENTION

The present invention is generally directed to the salt-stable cosmetic composition in the form of a low viscosity direct emulsion (oil in water) and method for manufacturing the same for enhancing skin, for example, by improving skin smoothness and radiance, minimizing pore appearance, reducing the appearance fine lines and wrinkles, brightening skin, reducing the effects of acne, and reducing one or more of dryness, tightness, dark spots, and inflammatory lesions or a combination of these.

BACKGROUND OF THE INVENTION

There are a variety of skin conditions that benefit from salt-stable cosmetic compositions that may be applied and left on the skin to brighten skin, reduce the effects of acne, and reduce one or more of dryness, tightness, dark spots, and inflammatory lesions, among other possible benefits. Many skin care products provide active ingredients that address one or more of these or other skin issues, yet there are challenges in providing products that have sufficiently high amounts of actives to confer the desired benefits. Products that include high amounts of actives are often formulated with a high content of oils, emulsifiers or thickeners to stabilize the actives. Such formulations can be heavy and leave a greasy skin feel or cause dryness or irritation.

Accordingly, there is a need in the art for the salt-stable cosmetic composition that offers light weight feel in a stable formulation that includes high amounts of actives for improving skin smoothness and radiance, minimizing pore appearance, reducing the appearance fine lines and wrinkles, brightening skin, reducing the effects of acne, and reducing one or more of dryness, tightness, dark spots, and inflammatory lesions or a combination of these.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In various embodiments, a composition is provided for use according to the invention that includes a direct fluid emulsion composition and method for manufacturing the same for improving skin smoothness and radiance, minimizing pore appearance, reducing the appearance fine lines and wrinkles, brightening skin, reducing the effects of acne, and reducing one or more of dryness, tightness, dark spots, and inflammatory lesions or a combination of these. The salt-stable cosmetic composition is in the form of a low viscosity emulsion (oil in water) and is especially stable at high electrolyte contents and includes a salt-stable polymeric system comprising a polymer blend such that the salt-stable cosmetic composition resists phase separation, pilling and gellifying at high salt content (greater than 2%), conferring a flowable, lightweight lotion-type texture.

The salt-stable cosmetic composition in the form of a direct oil in water emulsion includes water and oily phases. In some embodiments, the water phase includes a salt-stable polymeric system that includes polyacrylate crosspolymer-6, acrylamide/sodium acryloyldimethyltaurate copolymer, and one or more gum, wherein the total amount of polymer present in the salt-stable cosmetic composition is not more than about 1.5%, by weight, based on the total weight of the salt-stable cosmetic composition. The water phase also includes at least one acidic skin active present in the form of cosmetically acceptable acids, and one or more neutralizing agents present together with the at least one acidic skin active to provide a pH in a range from about 4.5 to about 7.5. The oil phase includes at least one oil, and at least one emulsifier. In the various embodiments, the salt-stable cosmetic composition also includes in the water phase one or more solvents comprising at least water.

In some embodiments, the water phase includes a salt-stable polymeric system that includes polyacrylate crosspolymer-6, present in a range from about 0.2% to about 1.2%, by weight, based on the total weight of the salt-stable cosmetic composition, acrylamide/sodium acryloyldimethyltaurate copolymer, present in a range from about 0.1% to about 0.4%, by weight, based on the total weight of the salt-stable cosmetic composition, and one or more gum, present in a range from about 0.1% to about 0.5%, by weight, based on the total weight of the salt-stable cosmetic composition, wherein the total amount of polymer present in the salt-stable cosmetic composition is not more than about 1.5%, by weight, based on the total weight of the salt-stable cosmetic composition.

In some embodiments, the water phase also includes one or more cosmetically acceptable acids, present in a range from about 4% to about 15%, by weight, based on the total weight of the salt-stable cosmetic composition, and a neutralizing agent present to provide a pH in a range from about 4.5 to about 7.5. In some particular embodiments, the neutralizing agent is present in a range from about 0.1% to about 5%, by weight, based on the total weight of the salt-stable cosmetic composition.

In some particular embodiments, the water phase includes a salt-stable polymeric system that includes polyacrylate crosspolymer-6, acrylamide/sodium acryloyldimethyltaurate copolymer, and sclerotium or xanthan gum.

In some embodiments, the salt-stable cosmetic composition may include a filler, for example boron nitride or methyl methacrylate crosspolymer, or a combination thereof.

In some embodiments, the at least one gum is selected from the group consisting of sclerotium gum, xanthan gum, cellulose gum, locust bean gum, carrageenan, and combinations thereof. In some particular embodiments, the at least one gum consists of sclerotium gum or xanthan gum.

In some embodiments, the salt-stable cosmetic composition includes salt present in the composition in an amount that is in a range from about 0.1% to about 4% by weight, based on the total weight of the composition. In some particular embodiments, salt is present in an amount that is greater than 2% by weight, based on the total weight of the composition.

In some embodiments, the cosmetically acceptable acid is selected from the group consisting of ascorbic acid, alpha hydroxy acid, beta hydroxy acid, and combinations thereof. In some embodiments, the cosmetically acceptable acid is selected from the group consisting of ascorbic acid, citric acid, lactic acid, glycolic acid, mandelic acid, salicylic acid, malic acid, azelaic acid, kojic acid, chlorogenic acid, ferulic acid, zinc PCA, gallic acid, hyaluronic acid, and combinations thereof.

In some embodiments, the neutralizing agent is selected from the group consisting of sodium hydroxide, potassium hydroxide, and combinations thereof.

In some embodiments, the at least one oil is selected from the group consisting of octyldodecanol, *Glycine soja* (soybean) oil, hydrogenated lecithin, isononyl isononanoate, isocetyl stearoyl stearate, dicaprylyl ether, isopropyl lauroyl sarcosinate, dicaprylyl carbonate, and combinations thereof.

In some embodiments, the at least one emulsifier is selected from the group consisting of liquid crystal emulsifiers, polysaccharide-based emulsifiers, hydrophobically-modified emulsifiers, and combinations thereof. In some embodiments, the at least one emulsifier is selected from the group consisting of C14-22 alcohols (and) C12-20 alkyl glucoside, octyldodecanol (and) octyldodecyl xyloside, and inulin lauryl carbamate, and combinations thereof.

In some embodiments the salt-stable cosmetic composition includes one or more water soluble solvents. In some embodiments, the one or more water soluble solvents is butylene glycol.

The salt-stable cosmetic composition may also include one or more additional ingredients selected from, but not limited to, phenylethyl resorcinol, chelating agents, other skin active components, antimicrobials and preservatives, fillers, antioxidants, fragrances, pearlescent agents, odor absorbers, coloring materials, essential oils, vitamins, and combinations of these.

In some embodiments, the salt-stable cosmetic composition includes one or more additives present in either the water or the oily phase, for example, including, but not limited to, the group consisting of tocopherol, phenylethyl resorcinol, sodium hyaluronate, caproyl salicylic acid, phenoxyethanol, hydroxyacetophenone, boron nitride, methyl methacrylate crosspolymer, trisodium ethylenediamine disuccinate, butylene glycol, caprylyl glycol, pentylene glycol, and combinations thereof.

In some embodiments, the salt-stable cosmetic composition excludes (i.e., is free from or essentially free from) one or all of the ingredients selected from the group consisting of gellan, stearic acid, waxes, plant butters over 5%, high levels of saturated fatty alcohols/acids above C16, ammonium acryloyldimethyltaurate/vp copolymer, hydroxyethyl acrylate/sodium acryloyldimethyl taurate copolymer, acrylates/beheneth-25 methacrylate copolymer, and combinations thereof.

The invention also provides in some embodiments a method for forming a salt-stable direct emulsion cosmetic composition. According to the method, the salt-stable cosmetic composition according to the invention is prepared by blending the polymer components of the salt-stable polymeric system of the water phase, adding the at least one acid, whereupon the blend typically appreciably thickens, and adjusting the pH to achieve a final pH in a range from about 4.5 to about 7.5, or more particularly from about 4 to about 7, or more particularly from about 5 to about 6, by the addition of a base such as sodium or potassium hydroxide.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

In the context of the invention, a direct emulsion is an oil in water emulsion.

As used herein, the term "instability" of a composition refers to separation of phases; watery texture; gellification of the salt-stable cosmetic composition; pilling or failure of some or all of the applied composition to soak into skin when applied and forming small globules or particles that collect on the skin's surface, and inability to be spread as a uniform emulsion when applied to a substrate. Instability can occur in compositions made outside of the scope of the disclosure (i.e., compositions lacking the salt stable polymer system), and compositions including too much polymer or too little salt.

The terms "Exclude, "Free" and "Essentially Free" means that no reliably measurable excluded material, for example, an excluded gellan and other gellifying agents, stearic acid, waxes, plant butters greater than about 5%, by weight, based on the total weight of the salt-stable cosmetic composition, and saturated fatty alcohols/acids above C16 present in amounts greater than about 2.5%, by weight, based on the total weight of the salt-stable cosmetic composition, or other excluded material as described herein, is present in the salt-stable direct emulsion cosmetic composition. The term "essentially free" means that, while it is preferred that no excluded material is present in the salt-stable direct emulsion cosmetic composition, it is possible to have very small amounts of the excluded material in the salt-stable direct emulsion cosmetic composition of the invention, provided that these amounts do not materially affect the advantageous properties of the salt-stable direct emulsion cosmetic composition. In particular, "essentially free" means that excluded material can be present in the salt-stable direct emulsion cosmetic composition at an amount of less than 5%, or less than 4%, or less than 3%, or less than 2%, or less than 1%, or less than 0.1% by weight, based on the total weight of the salt-stable direct emulsion cosmetic composition.

As shown herein, the inventors have provided the salt-stable cosmetic composition in the form of a direct oil in water emulsion includes water and oily phases. In some embodiments, the water phase includes a salt-stable polymeric system that includes polyacrylate crosspolymer-6, acrylamide/sodium acryloyldimethyltaurate copolymer, and one or more gum, wherein the total amount of polymer present in the salt-stable cosmetic composition is not more than about 1.5%, by weight, based on the total weight of the salt-stable cosmetic composition. The water phase also includes at least one acidic skin active present in the form of cosmetically acceptable acids, and one or more neutralizing agents present together with the at least one acidic skin active to provide a pH in a range from about 4.5 to about 7.5. The oil phase includes at least one oil, and at least one emulsifier. In the various embodiments, the salt-stable cosmetic composition also includes in the water phase one or more solvents comprising at least water.

The salt-stable cosmetic composition may also include one or more additional ingredients selected from, but not limited to, phenylethyl resorcinol, chelating agents, other skin active components, antimicrobials and preservatives, fillers, antioxidants, fragrances, pearlescent agents, odor absorbers, coloring materials, essential oils, vitamins, and combinations of these.

The surprising stability that is achieved with the salt-stable polymer system solves a key problem in the art relative to inclusion of efficacious levels of skin actives in a stable and aesthetically pleasing composition. According to the instant disclosure, such a composition is provided, wherein the lightweight oil in water emulsion provides a fresh and light feel upon application with a smooth, gliding texture that does not pill. The salt-stable composition has a low viscosity (i.e., it has a consistency that is thin like a serum or light lotion) with a high level of salt content (i.e., greater than 2%) and does not severely 'pill' (i.e., 'ball' or noodle') when applied to the skin. The salt-stable composition excludes other thickeners (i.e., solid waxes, structuring agents) to avoid building a cream-like consistency. Notably, the emulsion does not form a gel and does not phase separate into solid/liquid or oily and water based layers. These benefits are demonstrated to be directly dependent on controlled amounts of each of the polymer blend and cosmetically acceptable acid components in the salt-stable cosmetic composition, as further described herein.

In accordance with the various embodiments, it is contemplated that some or all of following ingredients would be excluded from the salt-stable cosmetic compositions used according to the invention: gellan and other gellifying agents, stearic acid, waxes, plant butters greater than about 5%, by weight, based on the total weight of the salt-stable cosmetic composition, and saturated fatty alcohols/acids above C16 present in amounts greater than about 2.5%, by weight, based on the total weight of the salt-stable cosmetic composition.

Accordingly, in various embodiments, the salt-stable composition is provided according to the following detailed description.

Salt Stable Polymeric System

Polymers

In accordance with the disclosure, the salt-stable cosmetic composition includes a salt-stable polymer system that includes at least three polymers for a water-based system, comprising polyacrylate crosspolymer-6, ammonium polyacryloyldimethyl taurate, and at least one gum selected from sclerotium gum, xanthan gum, cellulose gum, locust bean gum, and combinations thereof. The salt-stable polymer system expressly excludes gellan.

In some particular embodiments, the salt-stable polymer system that comprises polyacrylate crosspolymer-6, ammonium polyacryloyldimethyl taurate, and at least one gum selected from sclerotium gum, xanthan gum or a combination thereof. In some particular embodiments, the salt-stable polymer system consists of polyacrylate crosspolymer-6 ((commercially available from Seppic under the tradename SEPIMAX ZEN™), ammonium polyacryloyldimethyl taurate, and sclerotium gum. And in some particular embodiments, the salt-stable polymer system consists of polyacrylate crosspolymer-6, ammonium polyacryloyldimethyl taurate and xanthan gum.

In some embodiments, polyacrylate crosspolymer-6 may be present in a range from about 0.2% to about 1.2%, the acrylamide/sodium acryloyldimethyltaurate copolymer may be present in a range from about 0.1% to about 0.4%, and the one or more gum may be present in a range from about 0.1% to about 0.5%, all amounts by weight, based on the total weight of the salt-stable cosmetic composition, wherein the total amount of polymer present in the salt-stable cosmetic composition is not more than about 1.5%, by weight, based on the total weight of the salt-stable cosmetic composition.

In some embodiments, the total amount of polymer present in the salt-stable cosmetic composition is in an amount from about 0.3% to about 1.5%, or from about 0.5% to about 1.5%, or from about 1.0% to about 1.5%, or any suitable combination, sub-combination, range, or sub-range thereof by weight, based on the weight of the salt-stable cosmetic composition. One of ordinary skill in the art, however, will appreciate that other ranges are within the scope of the invention.

Thus, each one or the combination of polymers in the salt-stable cosmetic composition is present by weight, based on the total weight of the salt-stable cosmetic composition, as disclosed above from about 0.1, 0.2, 0.3, 0.4, 0.5, 0.6, 0.7, 0.8, 0.9, 1.0, 1.1, 1.2, 1.3, 1.4, to about 1.5 percent, including increments and ranges therein and there between.

Cosmetically Acceptable Acids (Acid Based Skin Actives)

In some embodiments, the water phase of the salt-stable cosmetic composition includes at least one or a combination of ascorbic acid or analogs thereof, alpha hydroxy acids, beta hydroxy acids, or other cosmetically acceptable acids, or any combination thereof. In some embodiments, the salt-stable cosmetic composition includes one or more acids selected from the group consisting of ascorbic acid, citric acid, lactic acid, glycolic acid, mandelic acid, salicylic acid, malic acid, azelaic acid, kojic acid, chlorogenic acid, ferulic acid, zinc PCA, gallic acid, hyaluronic acid, and combinations thereof. In some particular embodiments, the salt-stable cosmetic composition includes at least ascorbic acid.

The salt-stable cosmetic composition is a liquidous direct emulsion form that may be a rinse off or a leave on formulation, wherein the salt-stable cosmetic composition has a viscosity that is greater than that of water but is neither a gel or a cream and is thus flowable when applied, and may be provided infused into a suitable substrate.

In various embodiments, the total amount of cosmetically acceptable acid present in a range from about 4% to about 15%, by weight, based on the total weight of the salt-stable cosmetic composition, and a neutralizing agent present to provide a pH in a range from about 4.5 to about 7.5.

In various embodiments, the neutralizing agent is present in a range from about 0.1% to about 5%, by weight, based on the total weight of the salt-stable cosmetic composition.

In some embodiments, the salt-stable cosmetic composition includes salt (including salt provided by pH adjusting neutralizing agents, as further described herein) present in the composition in an amount that is in a range from about 0.1% to about 4% by weight, based on the total weight of the composition. In some particular embodiments, salt is present in an amount that is greater than 2% by weight, based on the total weight of the composition.

Thus, salt may be present by weight, based on the total weight of the salt-stable cosmetic composition, from about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2, 3, to about 4 weight percent, including increments and ranges therein and there between.

Ascorbic Acid

In accordance with some embodiments, the salt-stable cosmetic composition may comprise ascorbic acid, or Vitamin C.

Ascorbic acid may be provided by the addition of any reducing analog of ascorbic acid, such as D-isoascorbic acid or by the addition of other small reducing compounds such as, but not limited to, glutathione, L-cysteamine, and the like. Such forms would be expected to provide an equivalent composition to that claimed and are within the scope of the invention.

Ascorbic acid and its derivatives may be present in the salt-stable cosmetic composition in an amount from about 1% to about 15%, and in some embodiments, from about 4% to about 15%, and in some embodiments, from about 10% to about 15%, and in some embodiments, from about 8% to about 12%, and in some embodiments about 10%, or any suitable combination, sub-combination, range, or sub-range thereof by weight, based on the weight of the salt-stable cosmetic composition.

Thus, ascorbic acid, when present, may be present, by weight, based on the total weight of the salt-stable cosmetic composition, from about 1, 2, 3, 4, 5, 6, 7, 8, 9, 10, 11, 12, 13, 14, to about 15 weight percent, including increments and ranges therein and there between.

Alpha Hydroxy Acid

In accordance with some embodiments, the salt-stable cosmetic composition may comprise at least one alpha hydroxy acid.

Suitable alpha hydroxy acids include glycolic acid, lactic acid, tartaric acid, mandelic acid, citric acid, ester derivatives thereof and combinations thereof. Exemplary ester derivatives include ester compounds of lactic acid, such as methyl lactate, ethyl lactate, butyl lactate and, similarly, ester compounds of glycolic acid, tartaric acid, mandelic acid, citric acid. One particularly suitable alpha hydroxy acid is lactic acid. Lactic acid, or 2-hydroxypropanoic acid, is provided composition to provide enhanced exfoliation of the skin. In addition, lactic acid also boosts production of glycosaminoglycan (GAG) in the skin, improving the barrier function and moisturization of skin.

In some particular embodiments, the alpha hydroxy acid in the salt-stable cosmetic composition may include at least one of lactic acid, glycolic acid, tartaric acid, mandelic acid, and citric acid.

The salt-stable cosmetic composition may include a concentration of alpha hydroxy acid in a range from about 4% to about 15%, or from about 8% to about 14% or from about 9% to about 13%, or from about 10% to about 12%, or is about 10%, or any suitable combination, sub-combination, range, or sub-range thereof by weight, based on the weight of the salt-stable cosmetic composition. One of ordinary skill in the art, however, will appreciate that other ranges are within the scope of the invention. In accordance with some embodiments, the amount of alpha hydroxy acid present is not more than about 10%.

Thus, any one of or a combination of alpha hydroxy acid when present, may be present, by weight, based on the total weight of the salt-stable cosmetic composition, from about 4, 5, 6, 7, 8, 9, 10, 11, 12, 13, 14, to about 15 weight percent, including increments and ranges therein and there between.

Beta Hydroxy Acid

In accordance with some embodiments, the salt-stable cosmetic composition may include at least one beta hydroxy acid. In some particular embodiments, the salt-stable cosmetic composition may include a beta hydroxy acid comprising salicylic acid.

The term "beta-hydroxy acid" is understood to mean, according to the present invention, a carboxylic acid having a hydroxyl functional group and a carboxylic functional group separated by two carbon atoms. A beta hydroxy acid can be present in the salt-stable cosmetic composition in the form of the free acid and/or in the form of one of its associated salts (salts with an organic base or an alkali metal, in particular), especially according to the final pH imposed on the salt-stable cosmetic composition.

Suitable beta hydroxy acids include salicylic acid and derivatives thereof (including 5-n-octanoylsalicylic acid, salicylate, sodium salicylate, and willow extract), capryloyl salicylic acid, beta hydroxybutanoic acid, propionic acid, beta-hydroxy beata-methylbutyric acid, carnitine tropic acid, and trethocanic acid, and combinations of these.

And in some particular embodiments, the beta hydroxy acid in the salt-stable cosmetic composition may include at least one of salicylic acid and derivatives thereof (including 5-n-octanoylsalicylic acid, salicylate, sodium salicylate, and willow extract), capryloyl salicylic acid, beta hydroxybutanoic acid, propionic acid, beta-hydroxy beata-methylbutyric acid, carnitine tropic acid, and trethocanic acid.

The salt-stable cosmetic composition may include a concentration of beta hydroxy acid in a range from about 0.1% up to and not more than about 2% of beta hydroxy acid, by weight, based on the total weight of the salt-stable cosmetic composition. In some embodiments, the salt-stable cosmetic composition may include up to and not more than about 2%, or about 1.9% of beta hydroxy acid. In some embodiments, the salt-stable cosmetic composition may include up to and not more than about 1% of beta hydroxy acid. In accordance with some embodiments, the amount of beta hydroxy acid, if present is not more than about 0.40% to about 0.50%. In some embodiments, the salt-stable cosmetic composition may include from about 0.1% to about 1% of beta hydroxy acid, or from about 0.2% to about 2.0%, or from about 0.1% to about 1.5%, or from about 0.2% to about 1.5%, or from about 0.3% to about 1.0%, or from about 0.35% to about 0.75%, or from about 0.4% to about 0.5%, or is about 0.45%, or any suitable combination, sub-combination, range, or sub-range thereof by weight, based on the weight of the salt-stable cosmetic composition. One of ordinary skill in the art, however, will appreciate that other ranges are within the scope of the invention.

Thus, the at least one beta hydroxy acid, when present, may be present in the salt-stable cosmetic composition from about 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, to about 2.0 weight percent, including increments and all ranges and subranges therein and there between.

Gallic Acid

In accordance with some embodiments, the salt-stable cosmetic composition may include gallic acid.

Gallic acid (also known as 3,4,5-trihydroxybenzoic acid) is a trihydroxybenzoic acid, a type of phenolic acid, found in gallnuts, sumac, witch hazel, tea leaves, oak bark, and other plants. The chemical formula of gallic acid is $C_6H_2(OH)_3COOH$. It is found both free and as part of hydrolyzable tannins.

In accordance with some embodiments, gallic acid may be present in the salt-stable cosmetic composition n is in a range from about 1% to about 10%, or from about 2% to about 9%, or from about 3% to about 7%, or from about 4% to about 6%, or from about 4% to about 5%, or is about 5%, or any suitable combination, sub-combination, range, or sub-range thereof by weight, based on the weight of the composition. In accordance with some embodiments, the amount of gallic acid present is at least about 5% to about 10%.

Thus, gallic acid, when present, may be present, by weight, based on the total weight of the salt-stable cosmetic composition, from about 1, 2, 3, 4, 5, 6, 7, 8, 9, to about 10 weight percent, including increments and ranges therein and there between.

Ferulic Acid

In accordance with some embodiments, the salt-stable cosmetic composition may include ferulic acid.

Ferulic acid, which is a hydroxycinnamic acid that can be broadly found in giant fennel, the seeds of coffee, apple, artichoke, peanut, and oranges, as well as in both seeds and cell walls of commelinid plants (such as rice, wheat, oats, and pineapple). Like many natural phenols, it is a strong antioxidant that is very reactive toward free radicals and reduces oxidative stress.

In accordance with some embodiments, ferulic acid may be present in the salt-stable cosmetic composition in a range from about 0.1% to about 2.0%, or from about 0.2% to about 1.5%, or from about 0.3% to about 1.0%, or from about 0.35% to about 0.75%, or from about 0.4% to about 0.5%, or is about 0.5%, or any suitable combination, sub-combination, range, or sub-range thereof by weight, based on the weight of the composition. In accordance with some embodiments, the amount of ferulic acid present is at least about 0.5%.

Thus, ferulic acid, when present, may be present, by weight, based on the total weight of the salt-stable cosmetic composition, from about 0.10, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9 to about 2.0 weight percent, including increments and ranges therein and there between.

Zinc PCA

In accordance with some embodiments, the salt-stable cosmetic composition may include Zinc PCA. Zinc PCA is the Zinc salt of pyrrolidone carboxylic acid.

In accordance with some embodiments, the amount of Zinc PCA, when present in the salt-stable cosmetic composition, is from about 0.1% to about 2.0%, or from about 0.2% to about 1.5%, or from about 0.3% to about 1.0%, or from about 0.4% to about 0.8%, or is about 0.5%, or any suitable combination, sub-combination, range, or sub-range thereof by weight, based on the weight of the composition. In accordance with some embodiments, the amount of Zinc PCA present is not more than about 0.4% to about 0.8%.

Thus, Zinc PCA, when present in the salt-stable cosmetic composition, may be present, by weight, based on the total weight of the composition, from about 0.10, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9 to about 2.0 weight percent, including increments and ranges therein and there between.

Azelaic Acid

In accordance with some embodiments, the salt-stable cosmetic composition may include azelaic acid.

In the various embodiments, azelaic acid may be present in the salt-stable cosmetic composition in a range from about 0.5% to about 5% by weight, based on the weight of the salt-stable cosmetic composition, or from about 0.5% to about 3%, or from about 0.75% to about 1%, or from about 0.5% to about 2.5%, or from about 0.5% to about 0.75%, or any suitable combination, sub-combination, range, or sub-range thereof by weight, based on the weight of the salt-stable cosmetic composition. One of ordinary skill in the art, however, will appreciate that other ranges are within the scope of the invention.

Thus, azelaic acid, when present, may be present in the salt-stable cosmetic composition, by weight, based on the total weight of the salt-stable cosmetic composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, to about 3.0 percent, including increments and ranges therein and there between.

Phytic and Chlorogenic Acids

In accordance with some embodiments, the salt-stable cosmetic composition may include at least one of phytic acid or chlorogenic acid. Phytic acid is also known as phytate and is a six-fold dihydrogenphosphate ester of inositol (specifically, of the myo isomer), also called inositol hexakisphosphate (IP6) or inositol polyphosphate. At physiological pH, the phosphates are partially ionized, resulting in the phytate anion. Phytic acid is found naturally in plant seeds and is a storage form of phosphorus. Chlorogenic acid is also known as chlorogenate or 3-caffeoylquinate and belongs to the class of organic compounds known as quinic acids and derivatives. Chlorogenic acid is the ester of caffeic acid (a hydroxycinnamic acid related to ferulic acid, as described herein above) and (ÿ)-quinic acid.

Phytic acid may be present in the salt-stable cosmetic composition in an amount from about 0.5% to about 5%, and in some embodiments, from about 1% to about 4%, and in some embodiments, from about 1% to about 2%, or any suitable combination, sub-combination, range, or sub-range thereof by weight, based on the weight of the salt-stable cosmetic composition. As exemplified in the instant disclosure, the phytic acid raw material is provided at a dilution of 50% such that the exemplified percent, by weight, based on the weight of the salt-stable cosmetic compositions, in the salt-stable cosmetic composition are multiplied by 0.5 to obtain the final percent, by weight, based on the weight of the salt-stable cosmetic composition, of phytic acid.

Chlorogenic acid may be present in the salt-stable cosmetic composition in an amount from about 0.5% to about 1.5%, and in some embodiments, from about 1% to about 1.5%, and in some embodiments, from about 1.1% to about 1.2%, or any suitable combination, sub-combination, range, or sub-range thereof by weight, based on the weight of the salt-stable cosmetic composition.

Thus, in various embodiments, one or more of phytic and chlorogenic acid when present, may be present in the salt-stable cosmetic composition according to the disclosure, and each of the individual components in the ranges as described herein above, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28 to about 30 percent by weight, including increments and ranges there between.

Solvents

Water

In accordance with the various embodiments, water is present in the salt-stable cosmetic composition in a range from about 10% to about 95%, or from about 20% to about 85%, or from about 30% to about 80%, or from about 40% to about 75%, or from about 45% to about 65%, or any suitable combination, sub-combination, range, or sub-range thereof by weight, based on the weight of the salt-stable cosmetic composition. One of ordinary skill in the art, however, will appreciate that other ranges are within the scope of the invention.

Thus, water may be present by weight, based on the weight of the salt-stable cosmetic composition, from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90 to about 95 weight percent, including increments and ranges therein and there between.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the salt-stable cosmetic composition is adjusted based on the amount of cosmetically acceptable acid to be in a range from about 4.5 and 7.5, or from about 5 to about 7, or from about 5 to about 6 or from about 6 to about 7. The pH is adjusted to the desired value by addition of a base (organic or inorganic), for example sodium hydroxide, potassium hydroxide, or another suitable base, or combinations thereof.

Water-Soluble Solvents

In accordance with some embodiments, the salt-stable cosmetic composition may include at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), organic solvents, polyols, glycols, or mixtures thereof.

In some particular embodiments according to the disclosure, when present, a water-soluble solvent may include butylene glycol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In accordance with the various embodiments the amount of the at least one water-soluble solvent, when present, is from about 0.1% to about 25%, or from about 0.1% to about 2%, or from about 0.1% to about 1%, or from about 0.1% to about 0.8%, or from about 0.1% to about 0.5%, or from about 1% to about 20%, or from about 1% to about 10%, or from about 2% to about 8%, or any suitable combination, sub-combination, range, or sub-range thereof by weight, based on the weight of the salt-stable cosmetic composition. One of ordinary skill in the art, however, will appreciate that other ranges are within the scope of the invention. In some embodiments, the salt-stable cosmetic composition includes more than one water soluble solvent, each water soluble solvent present in an amount as set forth herein above, wherein each different water soluble solvent may be present within one of the ranges selected from the ranges set forth herein above.

Thus, each one or combination of water-soluble solvents, when present, may be present by weight, based on the total weight of the salt-stable cosmetic composition, from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

Oily Phase

Oil

In accordance with the various embodiments, the salt-stable cosmetic composition includes at least one oil. In some embodiments, the oil is generally immiscible in water. The oil may be selected from hydrocarbons, silicones, fatty alcohols, glycols and vegetable oils. The oil may include one or a combination of polar and non-polar oil. In some embodiments, the oil may be chosen from hydrocarbon-based oils from plants or of plant origin, mineral oil, ester oils, fatty alcohols containing from 12 to 26 carbon atoms, fatty acids containing from 12 to 26 carbon atoms and vinylpyrrolidone copolymers, and combinations thereof.

In accordance with some particular embodiments, the salt-stable cosmetic composition may comprise an emulsion that comprises one or more oils, alone or in combination, with one or more emulsifier (as described herein) wherein the emulsifier is present in an amount that is in the range from about 15% to about 40% of the total amount of oils present in the salt-stable cosmetic composition.

In some embodiments according to the disclosure, the at least one oil is selected from the group consisting of octyldodecanol, *Glycine soja* (soybean) oil, hydrogenated lecithin, isononyl isononanoate, isocetyl stearoyl stearate, dicaprylyl ether, isopropyl lauroyl sarcosinate, dicaprylyl carbonate, and combinations thereof, wherein octyldodecanol may be present in a range from about 0.5% to about 3.5%, and wherein *Glycine soja* (soybean) oil may be present in a range from about 0.1% to about 1%, and wherein hydrogenated lecithin may be present in a range from about 0.1% to about 1%, and wherein isononyl isononanoate may be present in a range from about 1% to about 5%, and wherein isocetyl stearoyl stearate may be present in a range from about 0.1% to about 0.5%, and wherein dicaprylyl ether may be present in a range from about 0.1% to about 0.5%, and wherein isopropyl lauroyl sarcosinate may be present in a range from about 0.5% to about 2%, and wherein dicaprylyl carbonate may be present in a range from about 0.5% to about 1.5%, all amounts, by weight, based on the weight of the total composition.

In some particular embodiments the at least one oil comprises a blend of at least two or more of the oils selected from the group consisting of octyldodecanol, *Glycine soja* (soybean) oil, hydrogenated lecithin, isononyl isononanoate, isocetyl stearoyl stearate, dicaprylyl ether, isopropyl lauroyl sarcosinate, dicaprylyl carbonate, and combinations thereof.

In some particular embodiments the at least one oil comprises a blend of oils comprising octyldodecanol, *Glycine soja* (soybean) oil, isononyl isononanoate, isocetyl stearoyl stearate, dicaprylyl ether, isopropyl lauroyl sarcosinate, dicaprylyl carbonate, and combinations thereof.

In some particular embodiments the at least one oil comprises a blend of oils comprising octyldodecanol, *Glycine soja* (soybean) oil, hydrogenated lecithin, isononyl isononanoate, isocetyl stearoyl stearate, isopropyl lauroyl sarcosinate, dicaprylyl carbonate, and combinations thereof.

As used herein, oil refers to any nonpolar compound that is a liquid at 25° C. and is hydrophobic and lipophilic. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa (10−3 to 300 mmHg). The term "non-volatile oil" relates to oil which remains on the skin or the keratin fiber, at room temperature and atmospheric pressure, for at least several hours and which in particular has a vapor pressure of less than 10−3 mmHg (0.13 Pa).

In accordance with the disclosure, by way of non-limiting example, the one or more oil in the salt-stable cosmetic composition may be chosen from botanical and essential oils, such as Helianthus Annuus Seed Oil, *Lavandula angustifolia* (lavender) Oil, Mentha Piperita Oil, *Rosmarinus officinalis* (rosemary) Leaf Oil Pelargonium Graveolens flower oil, *Citrus aurantium dulcis* (orange) peel oil, *Menthe viridis* (spearmint) leaf oil, *Citrus aurantifolia* (lime) oil, *Melaleuca alternifolia* (tea tree) leaf oil, *Citrus grandis* (grapefruit) peel oil, *Citrus medica limonum* (lemon) peel oil, rose flower oil, eucalyptus globulus leaf oil, and combinations thereof.

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The salt-stable cosmetic composition may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the salt-stable cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes (8×106 m2/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The salt-stable cosmetic composition may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The salt-stable cosmetic composition may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the salt-stable cosmetic composition may include a synthetic oil selected from the group consisting of hydrogenated polyisobutene and hydrogenated polydecene. A hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from C4 to C24, it being possible for these chains to be saturated or unsaturated and linear or branched; these oils are in particular wheat germ oil, sunflower oil, grape seed oil, sesame oil, corn oil, apricot oil, castor oil, rhea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 40 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ỹ 10, for instance Purcellin oil (cetearyl octanoate), isopropyl myristate, isopropyl palmitate, C12-C15 alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear C12-C13 alkyl) tartrates, such as those sold under the name Cosmacol ETI® by Enichem Augusta Industriale, and also di(linear C14-C15 alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC™ by Cognis;

(viii) fatty amides, such as isopropyl N-lauroyl sarcosinate, such as the product sold under the trade name Eldew SL 205™ from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

Hydrocarbon-based oils may be glyceride triesters and in particular to caprylic/capric acid triglycerides, synthetic esters and in particular isononyl isononanoate, oleyl erucate, C12-C15 alkyl benzoate, 2-ethylphenyl benzoate and fatty alcohols, such as octyldodecanol. As volatile hydrocarbon-based oils, mention is made of hydrocarbon-based oils containing from 8 to 16 carbon atoms and in particular of branched C8-C16 alkanes, such as C8-C16 isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C C8-C16 esters, and isohexyl neopentanoate.

In some embodiments, the salt-stable cosmetic composition may comprise one or more oils such as from those described herein above, and from oils that may be selected from branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some particular embodiments, suitable liquid alkanes that may be used according to the disclosure include hydrocarbon-based oils containing from 8 to 16 carbon atoms, and especially branched C8-C16 alkanes such as C8-C16 isoalkanes.

In some embodiments, the salt-stable cosmetic composition may comprise one or more oils selected from polar emollients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol % to about 350 g/mol.

In some embodiments, the salt-stable cosmetic composition may comprise polar emollients that include those derived from C12-050 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

The one or more oil, when present, alone or in combination as a blend of oils, may be present in the salt-stable cosmetic composition from about 0.0001% to about 20% or from about 0.001% to about 0.0010%, or from about 0.003% to about 0.004%, or from about 0.01% to about 0.1%, or from about 0.1% to about 10%, or from about 0.5% to about 20%, or from about 1% to about 10%, or from about 5% to about 10%, or from about 2% to about 7%, or from about 0.5% to about 2%, or from about 0.008% to about 0.01%, or from about 0.1% to about 0.2%, or from about 0.5% to about 2%, or from about or any suitable combination, sub-combination, range, or sub-range thereof by weight, based on the weight of the salt-stable cosmetic composition. One of ordinary skill in the art, however, will appreciate that other ranges are within the scope of the invention. In some embodiments, the salt-stable cosmetic composition includes more than one oil, each oil present in an amount as set forth herein above, wherein each different oil (such as, for example, plant oils and extracts with oils) may be present within one of the ranges selected from the ranges set forth herein above.

Thus, each of the at least one oil or combination of oils is present by weight, based on the total weight of the salt-stable cosmetic composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19 to about 20 percent, including increments and ranges therein and there between.

Emulsifier

In some embodiments, the salt-stable cosmetic composition includes at least one emulsifier chosen in an appropriate manner according to the emulsion being an oil in water emulsion. In some such embodiments, the blend of two or more emulsifiers comprises emulsifiers that are selected from only one of anionic emulsifiers, amphoteric/zwitterionic emulsifiers, non-ionic emulsifiers. In some embodiments, the blend of two or more emulsifiers comprises emulsifiers that are selected from at least two of anionic emulsifiers, amphoteric/zwitterionic emulsifiers, non-ionic emulsifiers. In some embodiments, the blend of emulsifiers comprises only two emulsifiers. In some embodiments, the blend of emulsifiers comprises three or more emulsifiers.

In some embodiments, the salt-stable cosmetic composition includes one, two, three or more emulsifiers. In some embodiments, the at least one emulsifier includes one or more of a liquid crystal emulsifier, for example C14-22 alcohols (and) C12-20 alkyl glucoside (commercially available from Seppic under the tradename MONTANOV™ L), a polysaccharide-based emulsifier such as a xyloside emulsifier, for example, octyldodecanol (and) octyldodecyl xyloside (commercially available from Seppic under the tradename FLUIDANO™ 20X), or a hydrophobically-modified emulsifier, for example, inulin lauryl carbamate (commercially available from Beneo Orafti under the tradename Inutec™ SP1).

In some particular embodiments according to the disclosure, the at least one emulsifier is selected from the group consisting of C14-22 alcohols (and) C12-20 alkyl glucoside, octyldodecanol (and) octyldodecyl xyloside, and inulin lauryl carbamate, and combinations thereof.

In some particular embodiments the at least one emulsifier comprises a blend of at least two or more of the emulsifiers selected from the group consisting of C14-22 alcohols (and) C12-20 alkyl glucoside, octyldodecanol (and) octyldodecyl xyloside, and inulin lauryl carbamate, and combinations thereof.

In some particular embodiments the at least one emulsifier comprises a blend of at least two or more of the emulsifiers selected from the group consisting of C14-22 alcohols (and) C12-20 alkyl glucoside, octyldodecanol (and) octyldodecyl xyloside, and inulin lauryl carbamate, and combinations thereof, wherein C14-22 alcohols (and) C12-20 alkyl glucoside may be present in a range from about 2% to about 5%, and wherein octyldodecanol (and) octyldodecyl xyloside may be present in a range from about 0.5% to about 3%, and wherein inulin lauryl carbamate may be present in a range from about 0.5% to about 3%, all amounts, by weight, based on the weight of the total composition.

In some particular embodiments the at least one emulsifier comprises C14-22 alcohols (and) C12-20 alkyl glucoside and inulin lauryl carbamate together with a blend of oils comprising octyldodecanol, *Glycine soja* (soybean) oil, hydrogenated lecithin, isononyl isononanoate, isocetyl stearoyl stearate, isopropyl lauroyl sarcosinate, and dicaprylyl carbonate. According to such embodiments, the C14-22 alcohols (and) C12-20 alkyl glucoside may be present at about 2% and inulin lauryl carbamate may be present at about 4%, and octyldodecanol may be present at about 2.3%, *Glycine soja* (soybean) oil may be present at about 0.6%, hydrogenated lecithin may be present at about 0.5%, isononyl isononanoate may be present at about 3%, isocetyl stearoyl stearate may be present at about 0.3%, isopropyl lauroyl sarcosinate may be present at about 1.5%, and dicaprylyl carbonate may be present at about 1.2%, all amounts, by weight, based on the weight of the total composition.

In some particular embodiments the at least one emulsifier comprises octyldodecanol (and) octyldodecyl xyloside and inulin lauryl carbamate together with a blend of oils comprising octyldodecanol, *Glycine soja* (soybean) oil, isononyl isononanoate, isocetyl stearoyl stearate, dicaprylyl ether, and isopropyl lauroyl sarcosinate, and dicaprylyl carbonate. According to such embodiments, the octyldodecanol (and) octyldodecyl xyloside may be present at about 2% and inulin lauryl carbamate may be present at about 4%, and octyldodecanol may be present at about 0.7%, *Glycine soja* (soybean) oil may be present at about 0.5%, isononyl isononanoate may be present at about 3%, isocetyl stearoyl stearate may be present at about 0.3%, dicaprylyl ether may be present at about 0.4%, and isopropyl lauroyl sarcosinate may be present at about 1.5%, dicaprylyl carbonate may be present at about 1%, all amounts, by weight, based on the weight of the total composition.

In accordance with some particular embodiments, the salt-stable cosmetic composition may comprise an emulsion that comprises one or more oils (as described herein), alone or in combination, with one or more emulsifier, wherein the emulsifier is present in an amount that is in the range from about 15% to about 40% of the total amount of oils present in the salt-stable cosmetic composition.

More generally, in some embodiments, the at least one emulsifier or combination thereof is present in the salt-stable cosmetic composition in an amount ranging from about 0.1% to about 15% by weight relative to the weight of the salt-stable cosmetic composition. In some embodiments, the at least one emulsifier is present in the salt-stable cosmetic composition in an amount ranging from about 0.5% to about 3.5% by weight, including increments and ranges therein and there between, based upon the total weight of the salt-stable cosmetic composition.

In some embodiments, one or more emulsifiers, alone or in combination, can be present in the salt-stable cosmetic composition, and in some embodiments, each emulsifier may be present from about 0.1% to about 5% by weight, from about 0.25% to about 2.5% by weight, from about 0.5% to about 1.8%, from about 0.5 to about 1.25%, and from about 0.5 to about 0.8%, or any suitable combination, sub-combination, range, or sub-range thereof by weight, based on the weight of the salt-stable cosmetic composition.

Thus, one or a combination of emulsifiers may be present, by weight, based on the weight of the salt-stable cosmetic composition, each one or the combination present from about 0.1, 0.2, 0.3, 0.4, 0.5, 0.6, 0.7, 0.8, 0.9, 1.0, 2, 3, 4, 5, 6, 7, 8, 9, 10, 11, 12, 13, 14, to about 15 weight percent, including increments and ranges therein and there between.

Other Ingredients

In accordance with the various embodiments, salt-stable cosmetic composition may further include additional ingredients, generally including, but not limited to, chelating agents, pH adjusters, skin actives, humectants, antioxidants, plant extracts, plant oils and butters, fragrances, pearlescent agents, odor absorbers, coloring materials, essential oils, vitamins, antimicrobials and preservatives, and combinations of these. Non limiting examples of some of these optional additional ingredients are provided herein below.

Chelating Agents

In some embodiments, one or more other components, such as chelating agents can be present in the salt-stable cosmetic composition, in amounts from about 0.01% to about 2% by weight, from about 0.02% to about 1.5% by weight, from about 0.02% to about 1%, from about 0.02% to about 0.5%, and from about 0.2 to about 0.4%, or any suitable combination, sub-combination, range, or sub-range thereof by weight, based on the weight of the salt-stable cosmetic composition. In some exemplary embodiments, chelating agents are selected from trisodium ethylenediamine disuccinate, ethylenediaminetetraacetic acid (EDTA), tetrasodium glutamate diacetate, tetrasodium etidronate, tetrasodium pyrophosphate, pentasodium ethylenediamine tetramethylene phosphonate, sodium staminate and combinations of these.

Thus, one or a combination of chelating agents may be present, by weight, based on the total weight of the salt-stable cosmetic composition, each one or the combination present from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 up to about 2 weight percent, including increments and ranges therein and there between.

Fillers

In accordance with some embodiments, the salt-stable cosmetic composition may comprise one or more fillers. The fillers may be of mineral or organic origin, natural or synthetic in nature in order to provide oil absorption or optical effects. Oil absorption fillers may impart a matte effect and non-greasy feeling onto the skin. Optical effects fillers may impart a soft-focus/haze/blur effect to the skin, provide the skin with a more uniform appearance, reduce the appearance of skin imperfections or discoloration, or reduce the visibility of pores.

In some particular embodiments according to the disclosure, when present, a filler may include boron nitride, methyl methacrylate crosspolymer, or a combination thereof. In accordance with such embodiments boron nitride may be present at about 0.6%, and methyl methacrylate crosspolymer may be present at about %, all amounts by weight, based on the total weight of the composition.

Some examples of oil-absorbing fillers include: mica, *Zea may* (corn) starch, magnesium oxide, nylon-12, nylon-66, cellulose, polyethylene, talc, talc (and) methicone, talc (and) dimethicone, perlite, sodium silicate, pumice, PTFE, Ammonium Polyacryloyldimethyl Taurate, polymethyl methacrylate, *Oryza sativa* (rice) starch, aluminum starch octenylsuccinate, potato starch modified, alumina, calcium sodium borosilicate, magnesium carbonate, hydrated silica, dimethicone/vinyl dimethicone crosspolymer, sodium carboxymethyl starch. According to one preferred embodiment, the oil-absorbing filler comprises spherical microparticles of porous silica having a mean particle size from 0.5 to 20 μm whose INCI name is silica sold by the company JCG Catalysts and Chemicals under the name Spheron L-1500. According to another preferred embodiment, the oil absorbing filler comprises hydrophobic aerogel particles whose INCI name is silica silylate sold by Dow Corning under the name VM-2270 Aerogel Fine Particles.

Some examples of optical effects fillers include: bismuth oxychloride, silica silylate, boron nitride, iron oxide, calcium carbonate, calcium sulfate (and) iron oxides, sodium potassium aluminum silicate.

Some examples of fillers which provide both oil-absorbing and optical effects include: silica, silica (and) methicone, silica (and) dimethicone, polysilicone-22, polysilicone-8, polysilicone-11, methyl methacrylate crosspolymer, polymethylsilsesquioxane, methylsilanol/silicate crosspolymer, vinyl dimethicone/methicone silsesquioxane crosspolymer, diphenyl dimethicone/vinyl diphenyl dimethicone silsesquioxane crosspolymer, and styrene/acrylates copolymer.

The filler may be present in the salt-stable cosmetic composition according to the invention, at a concentration, or from about 0.01% to 25%, or from about 0.01% to 0.5%, or from about 0.1% to 0.4%, or from about 0.2% to 0.3%, or from about 0.5% to 5.0%, or from about 1.0% to 5.0%, or from about 1.2% to 3.5%, or from about 1.0% to 2.5%, or from about 1.5% to about 2%, or from about 1.0% to about 1.8%, or from about 2.2% to 2.7% or from about 0.25% to about 0.4%, or any suitable combination, sub-combination, range, or sub-range thereof by weight, based on the weight of the salt-stable cosmetic composition. One of ordinary skill in the art, however, will appreciate that other ranges are within the scope of the invention. In some embodiments, the salt-stable cosmetic composition includes more than one filler, each filler present in an amount as set forth herein above, wherein each different filler may be present within one of the ranges selected from the ranges set forth herein above.

Thus, each one or combination of filler, when present, may be present by weight, based on the total weight of the salt-stable cosmetic composition, from about 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 to about 25.0 percent by weight, including increments and ranges there between.

Phenylethyl Resorcinol

In accordance with some embodiments, the salt-stable cosmetic composition may comprise phenylethyl resorcinol.

Phenylethyl resorcinol functions a tyrosinase inhibitor. The phenylethyl resorcinol, when utilized in the salt-stable cosmetic composition effectively whiten skin and reduce skin tone unevenness. Phenylethyl resorcinol has not shown adverse effects in basic toxicological tests, including acute oral toxicity, mutagenicity, skin irritation, skin sensitization, and phototoxicity.

In accordance with the various embodiments, when present, the amount of phenylethyl resorcinol present in the salt-stable cosmetic composition is from about 0.2% to about 2.0%, or from about 0.2% to about 1.5%, or from about 0.4% to about 1.0%, or from about 0.6% to about 0.9%, or from about 0.7% to about 0.8%, or from about 0.2% to about 0.8%, is about 0.75%, or any suitable combination, sub-combination, range, or sub-range thereof by weight, based on the weight of the salt-stable cosmetic composition. One of ordinary skill in the art, however, will appreciate that other ranges are within the scope of the invention. In accordance with some embodiments, the amount of phenylethyl resorcinol present is not more than about 0.2% to about 0.8%.

Thus, phenylethyl resorcinol, when present in the salt-stable cosmetic composition, is present, by weight, based on the total weight of the salt-stable cosmetic composition, from about 0.20, 0.30, 0.40, 0.50, 0.60, 0.70, 0.80, 0.90, 1.0, 1.1, 1.2, 1.3, 1.4, 1.5, 1.6, 1.7, 1.8, 1.9 to about 2.0 weight percent, including increments and ranges therein and there between.

Optional Actives and Other Ingredients

In some embodiments, there may be one or more optional actives or other ingredients (herein, "additives") present in the salt-stable cosmetic composition, the one or more additives selected from, for example, but not limited to: humectants, such as acetamide MEA, glycols, such as glycerin and propylene glycol; anti-microbials; antioxidants, including, but not limited to, phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin (Scutellaria Baicalensis root extract), pine bark extract (Pinus Pinaster bark/bud extract), ellagic acid; hyaluronic acid and its derivatives; hydroxyacetophenone;

and vitamins and vitamin derivatives, such as tocopherol and ascorbic acid; and combinations thereof.

In some embodiments, additives may include one or a combination of antimicrobial agents and their salts, for example, including, but not limited to, the group consisting of chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexandiol, and pentylene glycol, and combinations thereof.

In some embodiments, additives may include one or a combination of skin actives, for example, including, but not limited to, the group consisting of tocopherol, phenoxyethanol, sodium hyaluronate, capryloyl salicylic acid, phenylethyl resorcinol, hydroxyacetophenone, and combinations thereof.

In some embodiments, the one or more additives present in the salt-stable cosmetic composition may include one or more other components, for example, including, but not limited to, the group consisting of penetrants; sequestrants; fragrances; dispersants; ceramides; opacifiers and combinations thereof. Although the aforementioned optional components are given as an example, it will be appreciated that other optional components compatible with cosmetic applications known in the art may be used.

In accordance with the various embodiments, the amounts of additives, for example, actives and other components, present in the salt-stable cosmetic composition can range from about 0.001% to about 50%, from about 0.5% to about 30%, from about 1.5% to about 20%, and from about 5% to about 15%, or any suitable combination, sub-combination, range, or sub-range thereof by weight, based on the weight of the salt-stable cosmetic composition.

In some embodiments, one or more additives, alone or in combination, can be present in the salt-stable cosmetic composition from about 0.05% to about 50% by weight, from about 0.05% to about 2.5% by weight, from about 0.1% to about 2%, from about 0.25% to about 1.5%, and from about 0.5% to about 1.25%, or any suitable combination, sub-combination, range, or sub-range thereof by weight, based on the weight of the salt-stable cosmetic composition.

In some embodiments, one or more other components, such as preservatives, vitamins, preservatives, and the like, alone or in combination, can be present in the salt-stable cosmetic composition from about 0.05% to about 50% by weight, from about 0.05% to about 25% by weight, from about 0.1% to about 10%, from about 0.25% to about 5%, and from about 0.5 to about 3.5%, or any suitable combination, sub-combination, range, or sub-range thereof by weight, based on the weight of the salt-stable cosmetic composition.

Thus, one or a combination of additives may be present in the salt-stable cosmetic composition, by weight, based on the weight of the salt-stable cosmetic composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

EXAMPLES

Example 1: Raw Materials

Percentages of each ingredient as may be exemplified in the following composition examples are shown as amount of raw materials, wherein the raw materials may be present in an amount that is equal to the amount of active, or if the raw material has a concentration of active that is less than 100%, then the salt-stable cosmetic composition includes the raw material that includes active and a suitable solvent, wherein the concentration of active in the raw material is provided herein below in Table 1. If a RM is not listed in the table, it should be presumed to have an active concentration that is essentially 100% active.

TABLE 1

Select Raw Materials (including RMs having active concentrations of less than 100%)

| RM | Active | % Active in RM |
|---|---|---|
| ACRYLAMIDE/SODIUM ACRYLOYLDIMETHYL-TAURATE COPOLYMER (And) ISOHEXADECANE (And) POLYSORBATE 80 (SIMULGEL TM 600, from SEPPIC) | ACRYLAMIDE/ SODIUM ACRYLOYL-DIMETHYLTAURATE COPOLYMER | ~40% |
| Trisodium Ethylenediamine Disuccinate in Water (Natrlquest TM E30, from Innospec Active Chemicals) | Trisodium Ethylenediamine Disuccinate | ~37% |
| Inulin Lauryl Carbamate in Glycerin (INUTEC TM SL1, from CREACHEM) | Inulin Lauryl Carbamate | ~25% |
| Sclerotium Gum (Amigel TM Granule, from Alban Muller) | Sclerotium Gum | ~100% |
| Polyacrylate Crosspolymer-6 (Sepimax Zen TM, Seppic) | Polyacrylate Crosspolymer-6 | ~100% |

Example 2: Inventive Compositions

TABLE 2

Inventive Compositions

| Ingredient | Inventive 1 (Comp 6 in Table 3) | Inventive 2 (Comp 7 in Table 3) | Inventive 3 (Comp 8 in Table 3) | Inventive 4 |
|---|---|---|---|---|
| Polyacrylate Crosspolymer-6 | 0.80 | 0.40 | 1.20 | 0.40 |
| ACRYLAMIDE/SODIUM ACRYLOYLDIMETHYLTAURATE COPOLYMER (And) ISOHEXADECANE (And) POLYSORBATE 80* | 0.80 | 0.63 | 0.50 | 0.63 |

TABLE 2-continued

Inventive Compositions

| Ingredient | Inventive 1 (Comp 6 in Table 3) | Inventive 2 (Comp 7 in Table 3) | Inventive 3 (Comp 8 in Table 3) | Inventive 4 |
|---|---|---|---|---|
| Sclerotium Gum | 0.20 | 0.50 | 0.10 | |
| Xanthan Gum | | | | 0.50 |
| Ascorbic Acid | 10.00 | 10.00 | 10.00 | 10.00 |
| Sodium Hydroxide | 2.20 | 2.20 | 2.20 | 2.20 |
| Oil Blend (Octyldodecanol, *Glycine Soja* (Soybean) Oil, Isononyl Isononanoate, Isocetyl Stearoyl Stearate, Isopropyl Lauroyl Sarcosinate, Dicaprylyl Carbonate, Hydrogenated Lecithin) | 9.4 | | | |
| Oil Blend (Octyldodecanol, *Glycine Soja* (Soybean) Oil, Isononyl Isononanoate, Isocetyl Stearoyl Stearate, Isopropyl Lauroyl Sarcosinate, Dicaprylyl Carbonate, Dicaprylyl Ether) | | 7.4 | 7.4 | 7.4 |
| Fillers (Boron Nitride, Methyl Methacrylate Crosspolymer) | 1.5 | 1.5 | 1.5 | 1.5 |
| Emulsifier Blend (C14-22 ALCOHOLS (And) C12-20 ALKYL GLUCOSIDE, Inulin Lauryl Carbamate*) | 6.0 | | | |
| Emulsifier Blend (OCTYLDODECANOL (And) OCTYLDODECYL XYLOSIDE, Inulin Lauryl Carbamate*) | | 6.0 | 6.0 | 6.0 |
| Additives/Actives (Tocopherol, Sodium Hyaluronate, Phenylethyl Resorcinol, Hydroxyacetophenone, Capryloyl Salicylic acid, Phenoxyethanol) | 2.3 | 2.3 | 2.3 | 2.3 |
| Trisodium Ethylenediamine Disuccinate* | 0.30 | 0.30 | 0.30 | 0.30 |
| Caprylyl Glycol | 0.30 | 0.30 | 0.30 | 0.30 |
| Butylene Glycol | 3.00 | 3.00 | 3.00 | 3.00 |
| Water | 63.20 | 65.47 | 65.20 | 65.47 |

*Active is present at less than 100% of amount of RM.

Generally, inventive embodiments of the composition may include: polyacrylate crosspolymer-6 (~0.4-0.8%), acrylamide/sodium acryloyldimethyltaurate copolymer (~0.5-1.0%), sclerotium gum (~0.1-0.5%); ascorbic acid (~8-12%, or ~10%), sodium hydroxide (~1.8-3%, or ~2.2%); a blend of oils comprising octyldodecanol, *Glycine soja* (soybean) oil, isononyl isononanoate, isocetyl stearoyl stearate, isopropyl lauroyl sarcosinate, dicaprylyl carbonate, hydrogenated lecithin (total of ~9.4%), and a blend of emulsifiers comprising C14-22 alcohols (And) C12-20 alkyl glucoside, inulin lauryl carbamate (total of ~6%) OR a blend of oils comprising octyldodecanol, *Glycine soja* (soybean) oil, isononyl isononanoate, isocetyl stearoyl stearate, isopropyl lauroyl sarcosinate, dicaprylyl carbonate, dicaprylyl ether (total of ~7.4%), and a blend of emulsifiers comprising octyldodecanol (and) octyldodecyl xyloside, inulin lauryl carbamate (total of ~6%); fillers including boron nitride (~0.5%), methyl methacrylate crosspolymer (~1%) (total ~1.5%); other additives/actives comprising tocopherol (~0.5%), phenoxyethanol (~0.6%), sodium hyaluronate (~0.1%), capryloyl salicylic acid (~0.3%), phenylethyl resorcinol (~0.3%), trisodium ethylenediamine disuccinate (~0.3%), and hydroxyacetophenone (~0.5%), (total of 3.2%), and the balance water and other solvents comprising butylene glycol (~3%), and caprylyl glycol (~0.3%), (total of ~3.3%), the balance water. The foregoing represent some exemplary embodiments; other embodiments are possible consistent with the description set forth herein above.

Method of Preparing Inventive Composition:

In the various embodiments, the salt-stable cosmetic composition according to the invention is prepared by blending the polymer components of the salt-stable polymeric system of the water phase, adding the at least one acid, whereupon the blend typically appreciably thickens, and adjusting the pH to achieve a final pH in a range from about 4.5 to about 7.5, or more particularly from about 4 to about 7, or more particularly from about 5 to about 6, by the addition of a base such as sodium or potassium hydroxide.

Example 3: Comparative Compositions

Comparative compositions were prepared in which the combinations and/or amounts of polymers were varied, and in which the amounts/combination of polymers were maintained according to the invention and the amount of acid was increased to 15%. The specifics of the comparative compositions are shown in Table 3 and the text, below, wherein the comparative compositions are identified as Compositions 1-5 and 9-16 (Comp. 1-5 and 9-16).

TABLE 3

Comparative Compositions with varied polymer type/amount (Comp. 1-5 and 9-15)

| Comp. # | Polymer* | Other Ingredients |
|---|---|---|
| 1 | polyacrylate crosspolymer-6 (1%)<br>acrylamide/sodium acryloyldimethyltaurate copolymer (0.88%) | Ascorbic acid (10%)<br>Sodium hydroxide (2.2%)<br>Blend of oils<br>Blend of emulsifiers<br>Other additives |
| 2 | polyacrylate crosspolymer-6 (1%)<br>acrylamide/sodium acryloyldimethyltaurate copolymer (0.88%)<br>sclerotium gum (0.4%) | Ascorbic acid (10%)<br>Sodium hydroxide (2.2%)<br>Blend of oils<br>Blend of emulsifiers<br>Other additives |
| 3 | polyacrylate crosspolymer-6 (1%)<br>acrylamide/sodium acryloyldimethyltaurate copolymer (0.36%)<br>sclerotium gum (0.3%) | Ascorbic acid (10%)<br>Sodium hydroxide (2.2%)<br>Blend of oils<br>Blend of emulsifiers<br>Other additives |
| 4 | polyacrylate crosspolymer-6 (1%)<br>acrylamide/sodium acryloyldimethyltaurate copolymer (0.32%)<br>ammonium acryloyldimethyltaurate/vp copolymer (0.2%) | Ascorbic acid (10%)<br>Sodium hydroxide (2.2%)<br>Blend of oils<br>Blend of emulsifiers<br>Other additives |
| 5 | polyacrylate crosspolymer-6 (1%)<br>acrylamide/sodium acryloyldimethyltaurate copolymer (0.4%)<br>sclerotium gum (0.4%) | Ascorbic acid (10%)<br>Sodium hydroxide (2.2%)<br>Blend of oils<br>Blend of emulsifiers<br>Other additives |
| 9 | hydroxyethyl acrylate/sodium acryloyldimethyl taurate copolymer (0.5%)<br>acrylamide/sodium acryloyldimethyltaurate copolymer (0.6%)<br>sclerotium gum (0.4%) | Ascorbic acid (10%)<br>Sodium hydroxide (2.2%)<br>Blend of oils<br>Blend of emulsifiers<br>Other additives |
| 10 | hydroxyethyl acrylate/sodium acryloyldimethyl taurate copolymer (0.5%)<br>acrylamide/sodium acryloyldimethyltaurate copolymer (0.48%)<br>sclerotium gum (0.4%) | Ascorbic acid (10%)<br>Sodium hydroxide (2.2%)<br>Blend of oils<br>Blend of emulsifiers<br>Other additives |
| 11 | polyacrylate crosspolymer-6 (0.5%)<br>acrylamide/sodium acryloyldimethyltaurate copolymer (0.4%)<br>hydroxyethyl acrylate/sodium acryloyldimethyl taurate copolymer (0.5%) | Ascorbic acid (10%)<br>Sodium hydroxide (2.2%)<br>Blend of oils<br>Blend of emulsifiers<br>Other additives |
| 12 | polyacrylate crosspolymer-6 (1%)<br>acrylamide/sodium acryloyldimethyltaurate copolymer (0.32%)<br>ammonium acryloyldimethyltaurate/steareth-25 methacrylate crosspolymer (0.2%) | Ascorbic acid (10%)<br>Sodium hydroxide (2.2%)<br>Blend of oils<br>Blend of emulsifiers<br>Other additives |
| 13 | polyacrylate crosspolymer-6 (1%)<br>acrylamide/sodium acryloyldimethyltaurate copolymer (0.32%)<br>acrylates/beheneth-25 methacrylate copolymer (0.2%) | Ascorbic acid (10%)<br>Sodium hydroxide (2.2%)<br>Blend of oils<br>Blend of emulsifiers<br>Other additives |
| 14 | polyacrylate crosspolymer-6 (1%)<br>acrylamide/sodium acryloyldimethyltaurate copolymer (0.32%) | Ascorbic acid (10%)<br>Sodium hydroxide (2.2%)<br>Blend of oils<br>Blend of emulsifiers<br>Other additives |
| 15 | polyacrylate crosspolymer-6 (1%)<br>sclerotium gum (0.3%) | Ascorbic acid (10%)<br>Sodium hydroxide (2.2%)<br>Blend of oils<br>Blend of emulsifiers<br>Other additives |
| 16 | polyacrylate crosspolymer-6 (0.8%)<br>acrylamide/sodium acryloyldimethyltaurate copolymer (1.0%)<br>sclerotium gum (0.3%) | Ascorbic acid (15%)<br>Sodium hydroxide (3.3%)<br>Blend of oils<br>Blend of emulsifiers<br>Other additives |

*final concentrations

In one exemplary embodiment, a comparative composition (Comp. 16) having a relatively higher acid/salt content that was tested in comparison to exemplified embodiments of the inventive compositions includes the following ingredients in a composition having a pH of about 5-6: polyacrylate crosspolymer-6 (0.8%), acrylamide/sodium acryloyldimethyltaurate copolymer (1.0%), sclerotium gum (0.3%), ascorbic acid (15%), sodium hydroxide (3.3%), a blend of oils comprising octyldodecanol (~2.5%), *Glycine soja* (soybean) oil (~1%), hydrogenated lecithin (~0.5%), isononyl isononanoate (~3%), isocetyl stearoyl stearate (~0.5%), isopropyl lauroyl sarcosinate (~1.5%), and dicaprylyl carbonate (~1%), (total of 8.35%), a blend of emulsifiers comprising C14-22 alcohols (and) C12-20 alkyl glucoside (~1.5%), and inulin lauryl carbamate (~4%), (total of 5.6%), other additives/actives comprising tocopherol (~0.5%), phenoxyethanol (~0.5%), sodium hyaluronate (~0.1%), capryloyl salicylic acid (~0.5%), boron nitride (~0.5%), methyl methacrylate crosspolymer (~1%), phenylethyl resorcinol (~0.3%), trisodium ethylenediamine disuccinate (~0.3%), and hydroxyacetophenone (~0.5%), (total of 3.2%), and the balance water and other solvents comprising butylene glycol (~3%), caprylyl glycol (~0.5%), and pentylene glycol (~3%), (total of 6.3%).

Example 4: Demonstration of Stability Parameters

Samples of inventive and comparative compositions as described above were prepared and evaluated for stability and pilling upon application to a substrate. The results, as shown below, demonstrate that the selection of polymers and their amounts directly affect the stability of the composition and resistance to gelling and pilling.

Using the same example base formula as Comp. 16 (shown above), with 10% vitamin C, and adjusted to pH ~5.8, different polymeric thickeners were employed in combination, as shown in Table 4, below, and the tested compositions were screened for physical stability and for pilling potential during application.

Without being bound by theory, it is contemplated that in regards to the inventive compositions that did not demonstrate pilling or separate or gelling, the polyacrylate crosspolymer-6 adds yield and suspending power without adding too much viscosity, the acrylamide/sodium acryloyldimethyltaurate copolymer contributes to increase overall viscosity to ensure the salt-stable composition is not too watery thin, and the gum also increases body and stability of the salt-stable composition, especially when stability testing at elevated temperatures (data not shown). Certain other polymers were found to cause pilling even at relatively low levels, or did not increase viscosity at all.

TABLE 4

Stability Testing Results with Inventive and Comparative Compositions

| Comp. # | polymer 1 (conc %) | polymer 2 (conc %) | polymer 3 (conc %) | Result |
|---|---|---|---|---|
| 1 | polyacrylate crosspolymer-6 (1%) | acrylamide/sodium acryloyldimethyltaurate copolymer (0.88%) | n/a | Pilling |
| 2 | polyacrylate crosspolymer-6 (1%) | acrylamide/sodium acryloyldimethyltaurate copolymer (0.88%) | sclerotium gum (0.4%) | Pilling |
| 3 | polyacrylate crosspolymer-6 (1%) | acrylamide/sodium acryloyldimethyltaurate copolymer (0.36%) | sclerotium gum (0.3%) | Pilling |
| 4 | polyacrylate crosspolymer-6 (1%) | acrylamide/sodium acryloyldimethyltaurate copolymer (0.32%) | ammonium acryloyldimethyltaurate/ vp copolymer (0.2%) | Pilling |
| 5 | polyacrylate crosspolymer-6 (1%) | acrylamide/sodium acryloyldimethyltaurate copolymer (0.4%) | sclerotium gum (0.4%) | Pilling |
| 6 (Inventive) | polyacrylate crosspolymer-6 (0.8%) | acrylamide/sodium acryloyldimethyltaurate copolymer (0.32%) | sclerotium gum (0.2%) | Stable; no pilling |
| 7 (Inventive) | polyacrylate crosspolymer-6 (0.4%) | acrylamide/sodium acryloyldimethyltaurate copolymer (0.25%) | sclerotium gum (0.5%) | Stable; no pilling |
| 8 (Inventive) | polyacrylate crosspolymer-6 (1.2%) | acrylamide/sodium acryloyldimethyltaurate copolymer (0.2%) | sclerotium gum (0.1%) | Stable; no pilling |
| 9 | hydroxyethyl acrylate/sodium acryloyldimethyl taurate copolymer (0.5%) | acrylamide/sodium acryloyldimethyltaurate copolymer (0.6%) | sclerotium gum (0.4%) | Pilling |
| 10 | hydroxyethyl acrylate/sodium acryloyldimethyl taurate copolymer (0.5%) | acrylamide/sodium acryloyldimethyltaurate copolymer (0.48%) | sclerotium gum (0.4%) | Pilling, unstable |
| 11 | polyacrylate crosspolymer-6 (0.5%) | acrylamide/sodium acryloyldimethyltaurate copolymer (0.4%) | hydroxyethyl acrylate/ sodium acryloyldimethyl taurate copolymer (0.5%) | Pilling, very thin |
| 12 | polyacrylate crosspolymer-6 (1%) | acrylamide/sodium acryloyldimethyltaurate copolymer (0.32%) | ammonium acryloyldimethyltaurate/ steareth-25 methacrylate crosspolymer (0.2%) | Pilling |
| 13 | polyacrylate crosspolymer-6 (1%) | acrylamide/sodium acryloyldimethyltaurate copolymer (0.32%) | acrylates/beheneth-25 methacrylate copolymer (0.2%) | Pilling |
| 14 | polyacrylate crosspolymer-6 (1%) | acrylamide/sodium acryloyldimethyltaurate copolymer (0.32%) | n/a | Pilling, unstable |
| 15 | polyacrylate crosspolymer-6 (1%) | n/a | sclerotium gum (0.3%) | Pilling |

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9% — 11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

What is claimed is:

1. A salt-stable cosmetic composition in the form of an oil in water emulsion, comprising:
   a water phase including:
      (i) a salt-stable polymeric system comprising a polymer blend comprising polyacrylate crosspolymer-6, acrylamide/sodium acryloyldimethyltaurate copolymer, and one or more gum;
      (ii) at least one acidic skin active present in the form of a cosmetically acceptable acid; and
      (iii) one or more neutralizing agents to provide a pH in a range from about 4.5 to about 7.5; and
   an oil phase,
   wherein:
      the total amount of polymer present in the salt-stable cosmetic composition is not more than about 1.5%, by weight, based on the total weight of the salt-stable cosmetic composition;
      the salt stable cosmetic composition includes greater than 2% salt; and
      the salt-stable cosmetic composition resists phase separation, pilling and gellifying in comparison to an otherwise identical composition lacking the salt-stable polymeric system.

2. The salt-stable cosmetic composition according to claim 1, wherein the oil phase includes at least one oil and at least one emulsifier.

3. The salt-stable cosmetic composition according to claim 2, wherein the one or more gum is selected from the group consisting of sclerotium, xanthan gum or a combination thereof and wherein the at least one acidic skin active is selected from the group consisting of ascorbic acid, citric acid, lactic acid, glycolic acid, mandelic acid, salicylic acid, malic acid, azelaic acid, kojic acid, chlorogenic acid, ferulic acid, zinc PCA, gallic acid, hyaluronic acid, and combinations thereof.

4. A salt-stable cosmetic composition in the form of an oil in water emulsion, comprising:
   a water phase including:
      (i) a salt-stable polymeric system comprising:
         polyacrylate crosspolymer-6, present in a range from about 0.2% to about 1.2%, by weight, based on the total weight of the salt-stable cosmetic composition;

acrylamide/sodium acryloyldimethyltaurate copolymer, present in a range from about 0.1% to about 0.4%, by weight, based on the total weight of the salt-stable cosmetic composition; and one or more gum, present in a range from about 0.1% to about 0.5%, by weight, based on the total weight of the salt-stable cosmetic composition;

(ii) one or more cosmetically acceptable acids, present, in total, in a range from about 4% to about 15%, by weight, based on the total weight of the salt-stable cosmetic composition; and (iii) at least one neutralizing agent present to provide a pH in a range from about 4.5 to about 7.5; and an oil phase, wherein:

the total amount of polymer present in the salt-stable cosmetic composition is not more than about 1.5%, by weight, based on the total weight of the salt-stable cosmetic composition;

the salt stable cosmetic composition includes greater than 2% salt; and the salt-stable cosmetic composition resists phase separation, pilling and gellifying in comparison to an otherwise identical composition lacking the salt-stable polymeric system.

5. The salt-stable cosmetic composition according to claim 4, wherein the oil phase includes at least one oil and at least one emulsifier.

6. The salt-stable cosmetic composition according to claim 4, wherein the neutralizing agent is present in a range from about 0.1% to about 5%, by weight, based on the total weight of the salt-stable cosmetic composition.

7. The salt-stable cosmetic composition according to claim 4, wherein the at least one gum is selected from the group consisting of sclerotium gum, xanthan gum, cellulose gum, locust bean gum, carrageenan, and combinations thereof.

8. The salt-stable cosmetic composition according to claim 4, wherein the at least one gum is selected from the group consisting of sclerotium, xanthan gum or a combination thereof.

9. The salt-stable cosmetic composition according to claim 4, wherein the cosmetically acceptable acid is selected from the group consisting of ascorbic acid, citric acid, lactic acid, glycolic acid, mandelic acid, salicylic acid, malic acid, azelaic acid, kojic acid, chlorogenic acid, ferulic acid, zinc PCA, gallic acid, hyaluronic acid, and combinations thereof.

10. The salt-stable cosmetic composition according to claim 4, wherein the cosmetically acceptable acid is selected from the group consisting of ascorbic acid, alpha hydroxy acid, beta hydroxy acid, and combinations thereof.

11. The salt-stable cosmetic composition according to claim 4, further comprising a filler selected from the group consisting of boron nitride or methyl methacrylate crosspolymer, and a combination thereof.

12. The salt-stable cosmetic composition according to claim 4, wherein the neutralizing agent is selected from the group consisting of sodium hydroxide, potassium hydroxide, and combinations thereof.

13. The salt-stable cosmetic composition according to claim 5, wherein the at least one oil is selected from the group consisting of octyldodecanol, *Glycine soja* (soybean) oil, hydrogenated lecithin, isononyl isononanoate, isocetyl stearoyl stearate, dicaprylyl ether, isopropyl lauroyl sarcosinate, dicaprylyl carbonate, and combinations thereof.

14. The salt-stable cosmetic composition according to claim 5, wherein at least one emulsifier is selected from the group consisting of liquid crystal emulsifiers, polysaccharide-based emulsifiers, hydrophobically-modified emulsifiers, and combinations thereof.

15. The salt-stable cosmetic composition according to claim 5, wherein at least one emulsifier is selected from the group consisting of C14-22 alcohols (and) C12-20 alkyl glucoside, octyldodecanol (and) octyldodecyl xyloside, and inulin lauryl carbamate, and combinations thereof.

16. The salt-stable cosmetic composition according to claim 5, further comprising one or more water soluble solvents.

17. The salt-stable cosmetic composition according to claim 5, further comprising one or more additives present in either the water or the oily phase, selected from the group consisting of tocopherol, phenylethyl resorcinol, sodium hyaluronate, capryloyl salicylic acid, phenoxyethanol, hydroxyacetophenone, crosspolymer, trisodium ethylenediamine disuccinate, butylene glycol, caprylyl glycol, pentylene glycol, and combinations thereof.

18. The salt-stable cosmetic composition according to claim 5, wherein the salt-stable cosmetic composition excludes one or all of the ingredients selected from the group consisting of gellan, stearic acid, waxes, plant butters over 5%, high levels of saturated fatty alcohols/acids above C16, ammonium acryloyldimethyltaurate/vp copolymer, hydroxyethyl acrylate/sodium acryloyldimethyl taurate copolymer, acrylates/beheneth-25 methacrylate copolymer, and combinations thereof.

19. A method for forming a salt-stable direct emulsion cosmetic composition according to claim 1, the method comprising blending the polymers, adding the at least one cosmetically acceptable acid, whereupon the blend typically appreciably thickens, and adjusting the pH to achieve a final pH in a range from about 4.5 to about 7.5 by adding the one or more neutralizing agents.

* * * * *